(12) United States Patent
Tai

(10) Patent No.: US 7,857,763 B2
(45) Date of Patent: Dec. 28, 2010

(54) AUTOMATIC SIGNAL-OPTIMIZING TRANSDUCER ASSEMBLY FOR BLOOD FLOW MEASUREMENT

(76) Inventor: Alan Chi-Chung Tai, 5573 Glenoak Ct., San Jose, CA (US) 95129

( * ) Notice: Subject to any disclaimer, the term of this patent is extended or adjusted under 35 U.S.C. 154(b) by 1623 days.

(21) Appl. No.: 11/108,362

(22) Filed: Apr. 18, 2005

(65) Prior Publication Data

US 2006/0241459 A1 Oct. 26, 2006

Related U.S. Application Data

(60) Provisional application No. 60/651,371, filed on Feb. 8, 2005.

(51) Int. Cl.
*A61B 8/00* (2006.01)
(52) U.S. Cl. .................. 600/437; 600/468; 600/465; 600/454; 600/459; 600/462
(58) Field of Classification Search .................. None
See application file for complete search history.

(56) References Cited

U.S. PATENT DOCUMENTS

| 4,002,221 A | 1/1977 | Buchalter |
| 4,541,433 A | 9/1985 | Baudino |
| 4,556,066 A | 12/1985 | Semrow |
| 4,848,356 A | 7/1989 | Nakamura et al. |
| 5,070,880 A | 12/1991 | Gomez et al. |
| 5,105,815 A | 4/1992 | Hall et al. |
| 5,289,821 A | 3/1994 | Swartz |
| 5,379,770 A | 1/1995 | Van Veen |
| 5,390,675 A | 2/1995 | Sheehan et al. |
| 5,409,005 A | 4/1995 | Bissonnette et al. |
| 5,419,333 A | 5/1995 | Hagiwara et al. |
| 5,517,994 A * | 5/1996 | Burke et al. ............... 600/437 |
| 5,623,930 A * | 4/1997 | Wright et al. ............. 600/456 |

(Continued)

FOREIGN PATENT DOCUMENTS

WO  WO2008/042559 A2  10/2008

OTHER PUBLICATIONS

American Heart Association. Heart Disease and Stroke Statistics: 2004 Update. http://www.americanheart.org.

(Continued)

*Primary Examiner*—Long V Le
*Assistant Examiner*—Joel F Brutus
(74) *Attorney, Agent, or Firm*—George M. Steres

(57) ABSTRACT

The invention uses a transducer and ultrasound system to form and direct ultrasound beams through the blood stream that will detect the Doppler shift in frequency between the beams and the return echo off the blood. The transducer can be secured onto the surface of the patient's skin with a transducer housing holder. A 1-D transducer, subject to an optimized angle with respect to the blood vessel, will generate and direct ultrasound beams electronically through a blood vessel below the skin and analyze the received echo, searching for the maximum signal amplitude of the Doppler frequency shift from the blood. Furthermore, the device continuously controls the direction of the ultrasound beams to achieve maximum return signal amplitude. Then, the condition and trend of the blood flow is recorded and displayed continuously over the desired diagnostic interval the device is in use.

26 Claims, 20 Drawing Sheets

U.S. PATENT DOCUMENTS

| | | | |
|---|---|---|---|
| 5,844,140 | A | 12/1998 | Seale |
| 5,917,927 | A * | 6/1999 | Satake et al. ................ 382/110 |
| 6,682,483 | B1 * | 1/2004 | Abend et al. ................ 600/437 |
| 6,773,400 | B2 | 8/2004 | Njemanze |
| 2002/0028995 | A1 * | 3/2002 | Mault ......................... 600/437 |
| 2003/0153832 | A1 * | 8/2003 | Zumeris et al. ............. 600/437 |

OTHER PUBLICATIONS

Evans D., McDicken W., Skidmore R., Woodcock J. Doppler Ultrasound Physics, Instrumentation, and Clinical Applications. John Wiley & Sons Ltd., 1989.

G. R. Lockwood, et al. Real-Time 3-D Ultrasound Imaging Using Sparse Synthetic Aperture Beam Forming. IEEE Trans. Ultrason., Ferroelec. Freq. Contr., 45:980-987, 1998.

Meire H., Farrant P. Basic Ultrasound. John Wiley & Sons Ltd., 1995. Radiological Health Bulletin. vol. XXIV, No. 8. Aug. 1990.

J. Valabhji, R. Elkeles, Debate: Are surrogate end-point studies worth the effort? http://www.cvm.controlled-trails.com/content/1/2/72, 2000.

* cited by examiner

AUTOMATIC SIGNAL-OPTIMIZING TRANSDUCER ASSEMBLY FOR BLOOD FLOW MEASUREMENT

CROSS-REFERENCE TO RELATED APPLICATIONS

This application claims the benefit of provisional patent application Ser. No. 60/651,371 filed on Feb. 8, 2005 by the present inventor.

FIELD OF INVENTION

This invention relates to a medical ultrasonic measurement system and method utilizing auto-aligned ultrasound beams to optimize echoed signals for tracking blood flow conditions and blood vessel geometry measurements.

BACKGROUND

Development in ultrasound technology has become an essential tool to medical professionals for more accurate diagnoses of diseases and other health conditions in their patients. Due to the non-invasive nature of the ultrasound, such a tool is considerably safer than other diagnostic instruments, such as X-rays that use high energy electromagnetic radiation. The ultrasound system works as an imaging technique by sending a high-frequency sound wave through internal body parts and receives a return echo. Next, the return echo from the sound wave generates a corresponding image that may then be used for medical examination. Such a system, used as a diagnostic instrument, has proven to be valuable in the practice of medicine. Although extremely high power levels of ultrasounds, such as those used to treat kidney stones, may heat up the body, no known instance of harm or injury has resulted from exposure to the lower energy levels used for diagnostic ultrasound waves, thus indicating an excellent safety record, even after several decades of use [E]. In consideration of the benefits to using ultrasound technology, physicians and other medical professionals are more likely to prefer using ultrasound system as a screening and researching tool rather than any other existing systems, for example x-rays.

With the advent of micro-processor technology and recent developments in computing power, generating three-dimensional (3-D) images from ultrasound waves is now possible. For real three-dimensional (3-D) imaging with two dimension (2-D) transducers (e.g., 50×50 channels), developments have made such technology feasible mainly to academic research. 2-D transducers demand channels in the order of 1000s, for instance, and the number of channels is proportional to the cost, such that the higher the number of channels required, the costlier the equipment; thus using such a system for common monitoring purposes is a bit unrealistic. Furthermore, such a transducer would need to be roughly greater than the size of an ordinary computer mouse, and for a device of that size to be placed on a patient's body for a possibly long duration of time renders such 2-D transducers rather impractical. In short, due to such a 2-D system's complexity and costly equipment, use of it in the commercial environment has been quite limited. While a solution[C] to lift this limitation would be the application of 2-D sparse array (array with removed elements), an application which demand channels in the order of 100s, such systems are still considered too bulky and not cost-effective.

On the other hand, the commercial monitoring systems currently available employs a single or dual element transducer, which requires manual or at least motor-servo operator assistance in monitoring applications. Being highly dependent on a clinical professional's continuous attention on the monitoring application, such a system would be subject to human error. The disadvantages and limitations of the aforementioned systems create a need for a simpler, more compact and cost-effective ultrasound system. 1-D transducers require only channels in the order of 10s (rather than 1000s like 2-D transducers) and may be produced in a more compact size than the other systems. The 1-D system is cost-effective and small enough in size to make it practical to fasten to a patient's body, which makes this system user-friendly and feasible in the hospital and/or clinical environment as a patient monitoring device.

Doppler ultrasound technology serves many invaluable purposes to medical examination applications. Such applications include but are not limited to the detection and assessment of peripheral arterial diseases, and the detection of emboli (blood clots or other obstructions lodged in a blood vessel) that flow through the blood stream during open heart surgery or other cardiac-related operations. However, there are several drawbacks to the current Doppler ultrasound technology in use by most medical professionals. The current commercial Doppler ultrasound system works through an operator-held transducer that needs to be positioned manually. Though there are some devices employed for positioning and securing the transducer (5,105,815) to the body, the maximum Doppler signal can still be easily missed due to movements from either the operator or the patient. Even the mechanical servo (5,844,140), also used to search for the maximum signal, requires human control and therefore proves unreliable for long-term monitoring purposes.

Ultrasound technology, as applied to transcranial Doppler (TCD), also serves as an important and economical tool for physicians in diagnosing the conditions of patients suffering from stroke-related diseases and brain injuries. Likewise, TCD is useful in detecting vasospasms and blockages in blood vessels by measuring ultrasound Doppler shift related to fluctuation in blood flow velocities. Yet TCD examinations are not performed in the clinical and hospital setting as often as they should be due to the application being extremely operator-dependent. TCD examinations demand an exceptionally steady hand, and thus are still rather not practical or effective in general use. Additionally, the application demands continuous monitoring of patients by highly trained and costly professionals, which may in effect cause an increase in administration costs. Altogether, these drawbacks make an otherwise advantageous application of TCD to be, in practice, very inefficient. Consequently, there is a strong demand and need for an ultrasonic system that goes beyond the current TCD technology to provide more accurate, reliable Doppler information and also perform continuous monitoring on a patient during or after surgery.

Another application of ultrasound technology is the calculation of flow-mediated dilation (FMD), or the measure of the ability of an artery to relax in response to increases in blood velocity, which is essential for cardiovascular research and related clinical applications as FMD provides the data central for determining vascular health. FMD[F] data further assists in furnishing imperative insights into the pre-intrusive phase of the disease atherosclerosis and can detect early signs of the same as well.

The FMD calculation is the computation of the change in post-stimulus arterial diameter, which is typically expressed as the percentage of the baseline diameter before the reactive hyperemia. To measure FMD, an ultrasound wave first scans the brachial artery longitudinally. This is done by holding a transducer securely in place with a stereo tactic clamp. The transducer must be held manually in place for the entire duration of the procedure. Then, a clear section of the vessel must be identified and displayed by the ultrasound system. Manually, again, the maximal change in the Doppler signal is ascertained for purposes of calculating the distance between the opposite lumen-arterial interfaces. As the ultrasound scans are performed continuously on the brachial artery, a blood pressure cuff fastened around the patient's forearm distal is inflated repeatedly over a length of time (e.g., five minutes) then abruptly deflated to artificially generate a reactive hyperemia that will cause the brachial artery to dilate. Finally, the mean diameters of the brachial artery as measured before, during, and after the artificially generated reactive hyperemia are used to calculate the percentage increase in FMD. Patients suffering from coronary artery diseases (CAD), cardiovascular diseases, or diabetes mellitus (DM), when monitored by the manually and statically secured FMD system, normally produces lower values of FMD than healthy individuals; therefore, to effectively monitor and regulate their particular conditions, the constant monitoring of their FMD levels is vital.

In light of the importance of accurate techniques for measuring brachial FMD, a better alternative to the traditional manual assessments is greatly needed. Currently, FMD analysis is prone to human error as the manual assessment of the vessel's diameter is done through a visual inspection and manually aligning the transducer. Such manual assessment and alignment is subject to severe observer errors. Also, the measurements can be thrown off by movements from the patient. In calculation, the percentage increase in the measure of FMD is in the order of 10%, thus even a slight change of transducer alignment along the longitudinal direction could result in imprecision. An imprecision in calculation could then easily cause dangerous misinterpretations by the reader. For this reason among others, it is necessary to have a way in which the transducer can be fastened and kept on the patient steadily and continually while Doppler signals are monitored, unencumbered by the reader's or the patient's movements.

U.S. Pat. No. 6,682,483 discloses a device using Doppler ultrasound to monitor blood velocity data with 3-D imaging that can be used for long-term, unattended blood flow monitoring in medical applications. In one embodiment, the invention comprises of a pad and processor that collects the Doppler data in a 3-D region through an array of sonic transducer elements, locking onto and tracking the points in the three-dimensional space to locate maximum blood velocity. This invention is limited by its 3-D imaging process, which would require a larger transducer and thus not be easily attachable to a patient's body. The invention is further limited in that it uses Mono-pulse tracking technique, known in the radar industry to track objects in air using electromagnetic wave as a medium, which is inefficient and impractical in its implementation due to ultrasound's strong frequency-dependent attenuation and nonlinear propagation in the human body, skull and blood vessels. The prior art also does not produce strong enough signals to overcome the noises and attenuation that are associated with ultrasound imaging processes.

On the other hand, the present invention solves the aforementioned issues with current monitoring procedures because it has the capability of transmitting automatically-aligning ultrasound beams into a patient and thus obtains the optimized Doppler signal for remarkably accurate results. The function of said invention will prove indispensable to a cardiac surgeon during and post-operation because it provides immediate information to the surgeon regarding the patient's degree of recovery, potential risk factors for stroke and/or other related health complications. Additionally, blood flow measured by Doppler shifts rather than other forms of measurement is quantified more accurately, which will facilitate a more precise judgment of the patient's condition. For example, some patients run the risk of suffering strokes post-surgery due to embolism, a condition where arteries are blocked by emboli or blood clots that travel up to the brain. Stroke is a leading cause of serious, long-term disability in such patients and is furthermore the third leading cause of death in the United States, behind heart disease and cancer [A]. But the ongoing measurements taken from this invention can provide early detection of emboli and stroke symptom as it analyzes the patient's blood flow condition, which in turn allows the surgeon to take preventive measures before complications even arise and thereby reducing chances of permanent brain damage in such patients and even potentially saving such patients' lives.

SUMMARY

The invention uses a transducer and detector unit to form and direct ultrasound energy through the blood stream that will detect the Doppler shift in frequency between the beam and the return echo off the blood. To use the preferred embodiment of the invention, the transducer is secured onto the surface of the patient's skin with a transducer housing holder. An electronic generator and processing unit coupled to the transducer for transmitting ultrasound beams and receive and process returned echoes from the transmitted ultrasound energy. The 1-D transducer, subject to an optimized angle with respect to the blood vessel and patient's skin, will generate and direct ultrasound beams electronically through a blood vessel below the skin and analyze the received echo, searching for the maximum signal amplitude of the Doppler frequency shift from the blood. To prevent the emitted ultrasound beams from completely missing the Doppler signals that might otherwise occur, an automatic alignment of this system can effectively search for direction of the maximum rate return signal amplitude and stay at the corresponding angle for the purpose of more accurate monitoring. Furthermore, the device continuously controls the direction of the ultrasound beams to achieve maximum return signal amplitude. Then, the condition and trend of the blood flow is recorded and displayed continuously over the desired diagnostic interval the device is in use.

BRIEF DESCRIPTION OF THE DRAWINGS

The logistics of the present invention may be better understood by referencing the appended illustrations, charts and graphs. The numbered figures and the corresponding descriptions are as follows.

REFERENCE NUMERALS AND SYMBOLS

Figure 1:
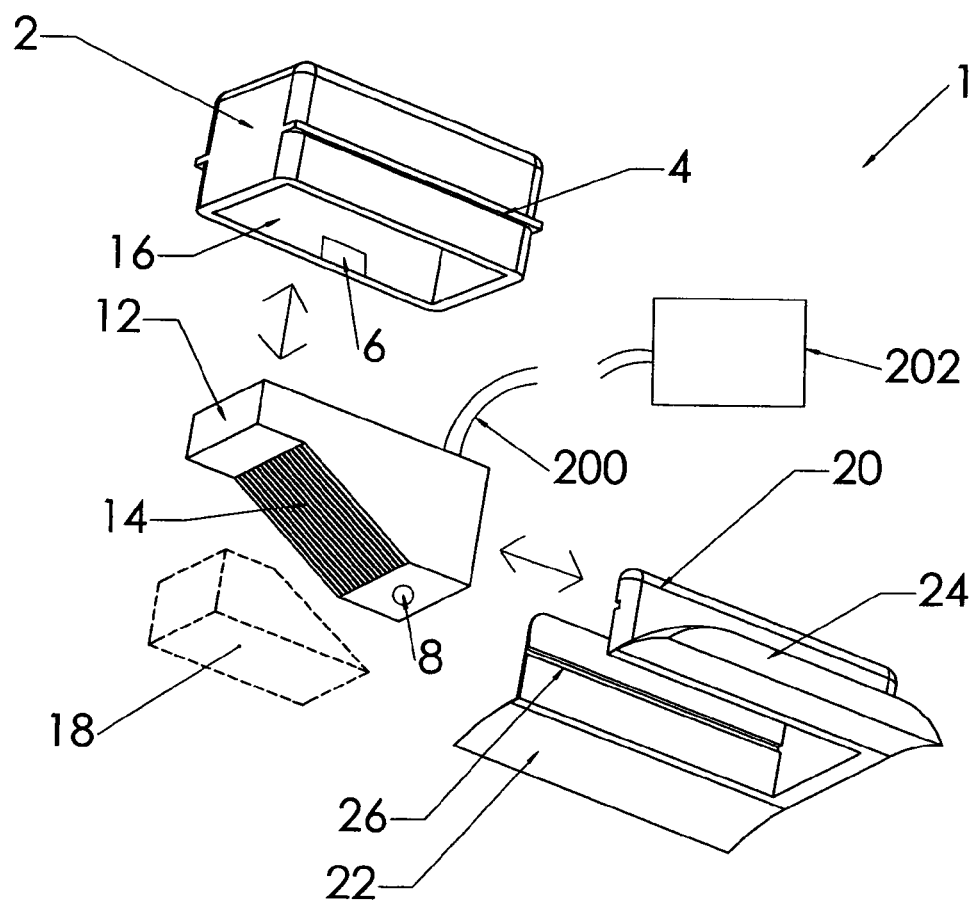
FIG. 1—Exploded perspective view of the ultrasound monitoring transducer

The following reference numerals indicate the parts and environment of the invention in the illustrations:

01—Present invention; Automatic signal-optimizing transducer assembly
02—Transducer housing
04—Ribs
06—Electrode
08—Thermal sensor
12—Transducer array body
14—Front face of transducer
15—Single element of the transducer with element width a
16—Gap; separation between transducer face and skin surface
18—Coupling agent
20—Transducer housing holder
22—Right extended wing
24—Left extended wing
25—Housing guide members
26—Insertion slots for ribs 04.
27—Opening for transmission/reception of ultrasound signals.
28—Blood vessel
29—Retaining tape member
30—Ultrasound beam
31—Adhesive material layer
32—Curved ceramic focusing
33—Dividing point for CW Doppler
34—Scanning plane
35—Out-of-plane direction
36—Surface of patient's skin
37—b (distance between blood vessel and transducer array)
38—r (half length of transducer element)
39—h (depth of blood vessel below skin)
40—Eye ball
42—Middle cerebral artery
44—Skull
45—Neck
46—Transducer array assembly with housing and cable
47—Left Carotid Artery
48—Right Carotid Artery
49—Electronic switch
50—Frontal window
52—Anterior window
54—Middle window
56—Posterior window
80, 82, 84—Ultrasound beams in different directions
90, 92, 94—Ultrasound beams in different directions of position A
100, 102, 104—Ultrasound beams in different directions of position B
130 to 146—Different steps of Acquisition and re-alignment mode and lock-in mode of FIG. 9
150 to 170—Different steps of Automatic Monitoring Mode of FIG. 10A
200, 202—signal connections, signal generating and processing unit
210—Inserted diagram of end view of a single element of transducer in FIG. 3
300 to 324—Different functional units of prior art ultrasound system
400—Incorporation of present invention into existing platform of ultrasound system
402—Implementation of Software upgrade of present invention
a element width for array of rectangular elements
α directivity angle of ultrasound energy from a single array element having width 'a'. (FIG. 3 for detail)
β fixed angle between array face 14 and skin mounting surface 36. (FIG. 5A).
γ elevation angle between axis of blood vessel and skin mounting surface 36. (FIG. 5B)
δ increment of scanning step angle ψ, deflection angle, in scanning plane, of ultrasound beam from normal direction of array face.
$\psi_{MAX}$ maximum ½ angle of beam deflection for an array with element width 'a'
$\psi_i, \psi_{i+1}, \psi_{i+2}$ successive values of deflected beam angle

DETAILED DESCRIPTION OF THE EMBODIMENTS

The purpose of the invention is to monitor and measure a medical patient's blood flow condition, using the Doppler ultrasound. To illustrate, the invention could be applied to the monitor of blood flow in carotid arteries inside the neck, which supply blood to the brain. An alternative embodiment of the invention could be applied to monitoring blood flow in the abdominal aorta, pulmonary arteries, the arteries in a patient's arms and legs, and other arteries in which ultrasound waves can be transmitted through the skin's surface.

FIG. 1 illustrates an exploded view of the monitoring transducer assembly 1. the assembly 1 has three major components; a housing 2, an ultrasound transducer array body 12 and a transducer housing holder 20. Housing 2 supports and protects a transducer array body 12 so the array 12 faces away from the housing through an opening gap 16. The housing 2 has protruding longitudinal flanges or ribs 4 on opposite sides that fit slidingly into opposing longitudinal slots 26 formed on the inside of corresponding opposite sides of the holder 20. The ribs 4 and slots 26 are formed so the housing can be mounted and demounted from the holder 20 by aligning the ribs with the slots, then sliding the housing (with the transducer mounted inside) from the front of the holder to the back.

The housing is retained in the holder by one of a number of releasable attachment means, such as friction between flanges and slots, or by other, known means: adhesive tape, straps, or hook and loop materials and the like. The flanges 4 and the corresponding slots 26 provide an expedient way for the transducer to be removed from the transducer housing holder 20.

Signal connections 200 are provided to system unit 202 for communicating ultrasound-generating signals to the transducer array 14 and communicating reflected ultrasound echo signals received by the array 14 back to the system unit 202 for processing, analysis and display and control.

To use the proposed embodiment of the invention, ultrasound waves are generated by the transducer array assembly 14 mounted into the housing holder 20 that is secured to the patient's neck near the carotid artery, for example. Ultrasound waves from the array 12 then travel through the neck and are reflected off moving blood cells inside the carotid artery reflected sound waves, return to the transducer at frequencies different from the frequency at which the ultrasound energy was emitted, and are then detected by the transducer array. The change in the frequency of the reflected sound waves relates to the speed of the blood cells from which they were reflected, thus can constitute an accurate gauge of the patient's blood flow. Such measurement can further indicates the direction of the blood flow, whether it is moving toward or away from the transducer.

As illustrated in FIG. 1 and FIGS. 2 A-D, the transducer housing holder 20 has two extended wings on opposite sides 22 and 24. These extended wings may arch slightly to complement the curve on the human neck or alternatively can be shaped to complement another body part. Adhesives material 31 (FIG. 2C) along the underside of the extended wings 22 and 24 fasten the apparatus securely to the patient's neck, for example. If a break from a monitoring cycle is desired, the housing and transducer array 2 and 12 respectively can be slid out of the transducer housing holder 20 and removed; meanwhile the holder 20 will remain attached to the skin of the patient so that other procedures may be performed without the interference of cables and wires attached to the transducer and housing. The assemblies 2 and 12 may be slid back into place at a later time when the monitoring cycle resumes.

Figure 2A:
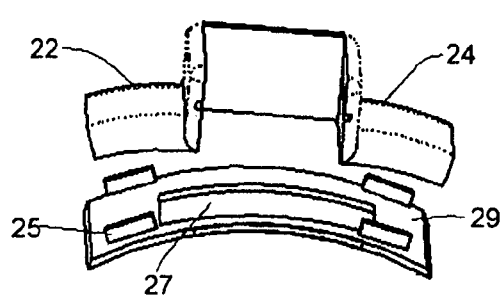
FIG. 2A—One view of the transducer housing holder attached to the retaining tape FIG. 2B—Second view of the transducer housing holder attached to the retaining tape FIG. 2C—Third view of the transducer housing holder attached to the retaining tape FIG. 2D—Fourth view of the transducer housing holder attached to the retaining tape FIG. 3—Schematic view of the transducer array assembly's relative position with the blood vessel FIG. 4—Perspective view of the curved ceramic focusing along the scanning plane FIG. 5A—Geometrical view of the transducer array assembly with respect to blood vessel in parallel to skin FIG. 5B—Geometrical view of the transducer array assembly with respect to blood vessel at an elevation angle y to skin FIG. 6—Graph of angle θ (x-coordinate) to merit value (y-coordinate)
Figure 2B:
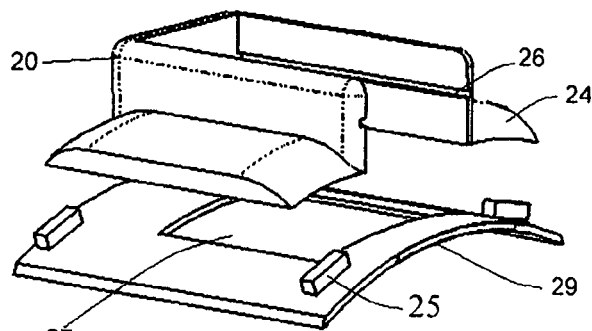
Figure 2C:
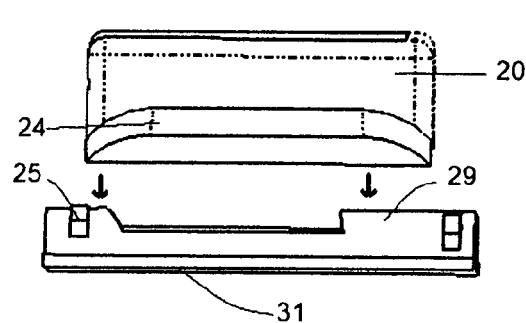
Figure 2D:
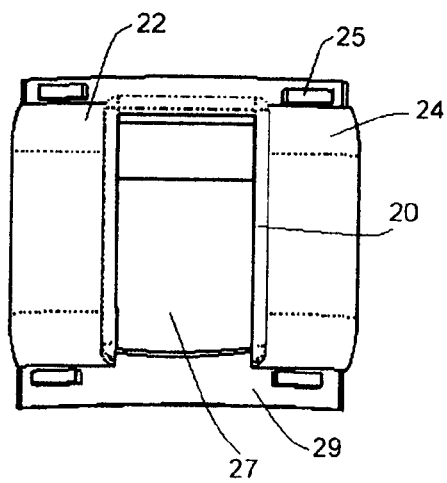

An alternative embodiment of the invention has the transducer housing holder 20 attached to the patient through the use of magnetic wings 22 and 24 and a magnetically active metal retaining tape 29 (FIG. 2A). The outer surface of the retaining tape 29 is made of a magnetically active metal, the inner surface of the tape 31 being an adhesive layer (FIG. 3C) for attaching to the patient's skin. In this embodiment, the extended wings 22, 24 are made of magnetic material that is attracted to the metallic tape 29. The retaining tape 29 will be attached to the extended wings 22 and 24 through magnetic attraction. Additionally, there is an opening, denoted by numeral 27, in the retaining tape 29 to allow the ultrasound beam from the array 14 to go through a coupling agent 18 (FIG. 1) into the patient. Logically, the magnetic side of the tape will attach itself to the magnetically charged wing and the adhesive side of the tape will secure the housing holder 20 to the patient's skin. The magnetic force between the one side of the retaining tape 29 and the extended wing is enough to hold the apparatus in place while it is being used and yet, because it is taped to the patient's skin by adhesive, the entire device may be removed and replaced with little effort.

Four guide 25 (FIG. 2B, C, D) are located on the four corners of the retaining tape 29. They are to further constrain the housing holder 20 in one direction while allowing the holder 20 to slide to and fro in the orthogonal direction, so that an optimized holder position can be located manually once the retaining tape is fixed.

When properly assembled, the inside of the housing between the face of the array 14 and the patient's skin is preferably filled with acoustic gel 18. An acoustic gel, composed primarily of water, is typically used as a transmission modifying agent to allow the ultrasound wave to better penetrate through to the patient's blood vessel. Normally, the gel 18 is spread between the transducer element and the surface of the skin where the ultrasound system is to be placed. In this application with the present invention, gel 18 represented by the dash line in FIG. 1, and is shaped by the inside of housing 2, front face of transducer 14, and the patient's skin 36. The gel 18 can further act as a thermal buffer between the transducer 14 and the patient's skin, thus mitigating any potential side effects the transducer-generated heat might have on the patient.

The merit of this is most apparent in the monitoring of critically ill patients who have little or no sensitivity or response to heat on their bodies. Nonetheless, as an option, one or more thermal sensors (8 in FIG. 1) (e.g., thermostats and the like) can be set near the front portion of the transducer while in the housing holder 20. Such sensor can send temperature data to the system unit 202 to reduce the transmission power in the event the sensor's temperature indicates it exceeds the patient's comfort level (e.g., above forty degrees Celsius).

Although use of acoustic gel 18 would be ideal since the gel has less attenuation, or reduction in strength of ultrasound waves, than alternative substances such as RTV or polyurethane, acoustic gel does not necessarily need to be used. The gap could also be filled by another type of transducer coupling agent 18, for example, such as the clear sparkling gels coupling agent described in U.S. Pat. No. 4,002,221, manufactured by Pharmaceutical Innovations, Inc. The nature of this coupling agent's composition adds to its efficacy in three major ways: (1) the water-based substance is less likely to irritate sensitive skin; (2) the gel will not corrode the transducer element, even after frequent use; and (3) the viscous nature of the gel will keep it from leakage and also ensures the substance to be slow to dry, thus able to withstand even prolonged usage. To use the clear sparkling gels transducer coupling agent with the invention, the material may be pre-cut to complement the shape the gap leaves between the housing 2 and the transducer 12. This custom-shaped material may then be inserted into the gap and use of the apparatus can then proceed.

Referring now to FIG. 1, a further embodiment of detecting the gel's usefulness is to add electrode 6 in the inside walls. Pair of electrodes can be put near the front end of the inner housing 2 facing each other. As the ultrasound gel or coupling agent is used for monitoring purpose, its water content tends to vaporize, resulting in lower conductivity. The electrodes 6 placed inside the inner wall are opposite to each other and are connected through connections 200 back to the system 202.

Once the conductivity reading from the sensors 6 indicates that the water content is low, a warning sign or alert signal can be triggered to inform the need of changing to a new ultrasound gel or coupling agent.

Figure 3:
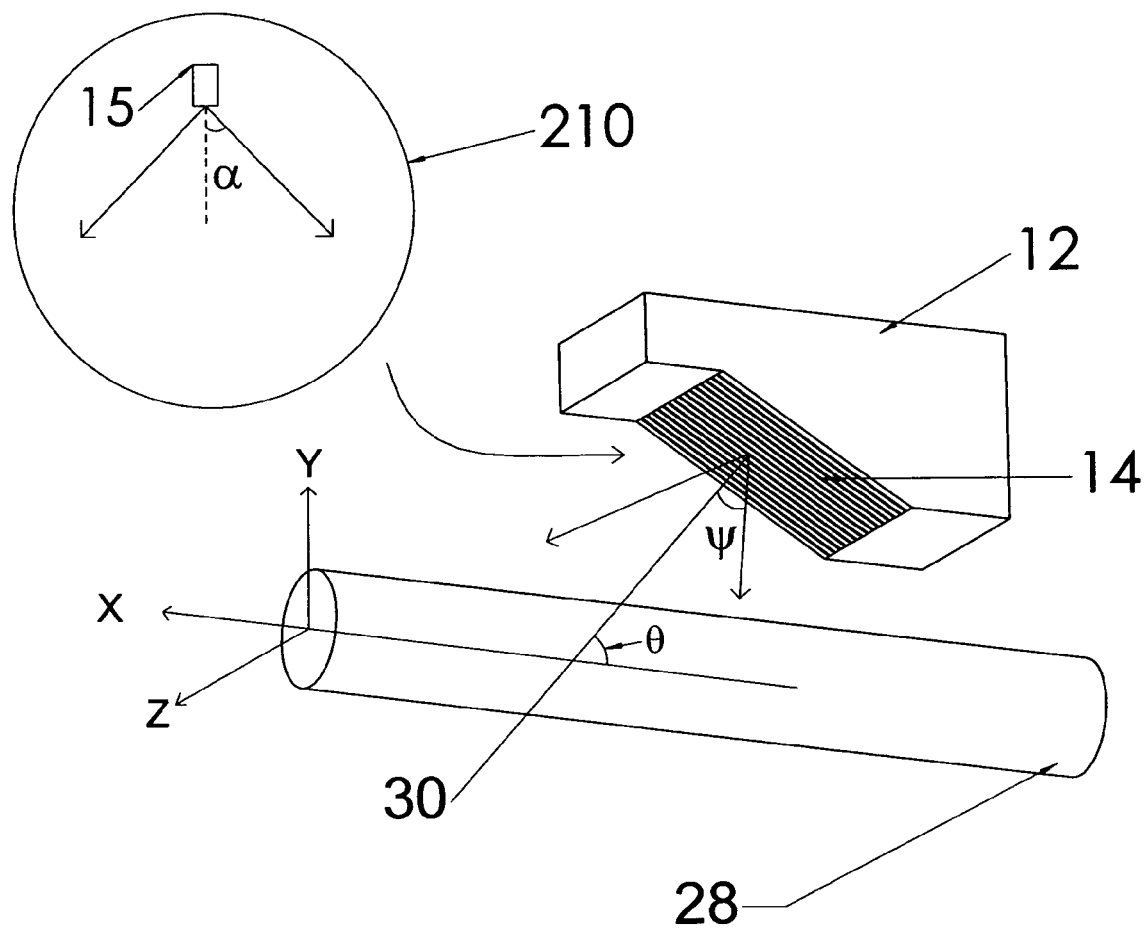

Note the following equation, as related to the acoustic energy radiation in the medium from a single element of transducer array as shown in the inserted diagram 210 of FIG. 3.

$$E(\alpha) = \frac{\sin(a\pi/\lambda \sin\alpha)}{(a\pi/\lambda)\sin\alpha} \qquad \text{EQUATION 1}$$

where λ is the wavelength of sound in the medium
a is the element width of the transducer array
α is the directivity angle of the transducer element Refering to FIG. 3 again, the transducer array assembly 12 is composed of an array of piezo-electric materials where the width "a" of the element 15 along the transducer face 14 ranges from approximately one wavelength to half a wavelength of the element's resonant frequency. In the Equation 1, the angle a means the angle at which the ultrasound beam 30 can be deflected across the scanning plane (YZ plane in FIG. 3), is determined by "a". To exemplify this, a phased array with an element width "a" equal to one half a wavelength (λ/2) can deflect an ultrasound beam at a deflecting angle up to +/−45 degrees. Likewise, a linear array with an element width "a" greater than one half of a wavelength will have a smaller, more acute deflecting angle. The deflecting angle will be dependant on its element width. As the variable "a" of the element increases, the deflecting angle for acoustic energy calculated from EQUATION 1 becomes narrower in space, consequently causing a reduction in the deflecting capabilities of the ultrasound in such a proportion where the smaller the angle, the smaller the deflecting capabilities of the ultrasound system.

The crystalline material in the ultrasound array typically consists of piezo-electric materials, such as Navy Type VI and Navy Type V of Lead Zirconate Titanate (PZT), as manufactured by Piezo Kinetics Corporation. Alternatively, the material can be made up of single crystal ferroelectrics, such as PZN, which has a higher piezo-electric coupling coefficient. This allows for superior performance of the transducer, even more so than that allowable by materials made up of PZT. In the past, the lack of homogeneity in the composition of the PZN material and the existence of micro-cracks or dislocations reducing the material's piezo-electric performance greatly limited its use. However, a surge in research and study on PZN has prompted much improvement in the productivity of single crystal ferroelectrics material. Such improvements have become advanced enough to build transducer arrays in the manufacturing environment which yield outstanding performance. The application of this material in transcranial Doppler (TCD) that requires high piezo-electric coupling coefficients has proven to be particularly useful in improving signal and noise ratio, especially in instances where there would otherwise be strong attenuation of ultrasound signals, such as in cases of transmitting ultrasound beams through the skull.

In one preferred embodiment of the invention, the ultrasound beam from the transducer will be generated by voltage sent through conducting wires and across the piezo-electric materials, which will then cause the material to vibrate at its resonant frequency, creating the ultrasound beam. Along the backside of the array, an epoxy-base-backing material will dampen the vibrating mode of the piezo-electric ceramic to prevent the piezo-electric ceramic from oscillating for too long. This backing material, made of an epoxy with characteristically low density and low sound velocity, is set such that it will have a low acoustic impedance Z to reflect an ultrasound wave traveling backward to return to the front. The low density and low sound velocity assists in increasing the sensitivity of the transducer, narrowing the bandwidth, and thus making such a material suitable for Doppler application. Along the front of the crystal will be a multiple matching layers, which thickness related with the wavelength of the ultrasound wave, are used for the purpose of matching the acoustic impedance Z of the piezo-electric ceramic (or high Z) to the patient's body (low Z) in such a manner that the ultrasound energy created will be more effective in propagating into the patient's body.

This transducer array is interconnected to the main 200 cable through a strain relief located at the back of the housing 2. This strain relief would be glued to the jacket of the main cable and would have enough flexibility to the material to provide relief of pressures incurred from the bending of the main cable. The function of the strain relief is to protect the cable interface along the housing. The main cable will consist of a bundle of small coaxial cables where each of such cables will connect to the corresponding element. This shall be accomplished through a flex circuit or circuit board assembled with the module.

The transducer array assembly 12 is encased inside the housing 2 and shielded by the base of the small coaxial cables. Internal shielding of the main cable will minimize interferences from electrical noises in the environment. Even if the module consists of 50 coaxial cables, the diameter of the main cable can be made smaller than half a centimeter and be pliable and small enough to make such a device easy to use and also comfortable for the patient. A number of present medical cable companies manufacture this type of miniature cable, such as the Precision Interconnect Division of Tyco Electronics.

Further aspects of the invention will become apparent from consideration of the drawings and the ensuing description of preferred embodiments of the invention. For instance, refer again to FIG. 1. The preferred elements of the transducer array 12 are to be equal in width and rectangular in shape. In operation, piezo-electric materials in the elements will emit ultrasound beams perpendicular to the elements and its sequence of scanning will be controlled by an electronic ultrasound system computer in the system unit 202. In FIG. 3, ultrasound beams 30 are transmitted and scanned from one side of the array 14 to the other, perpendicular to the face of array 14 along the z-direction of the transducer face 14.

Figure 17:
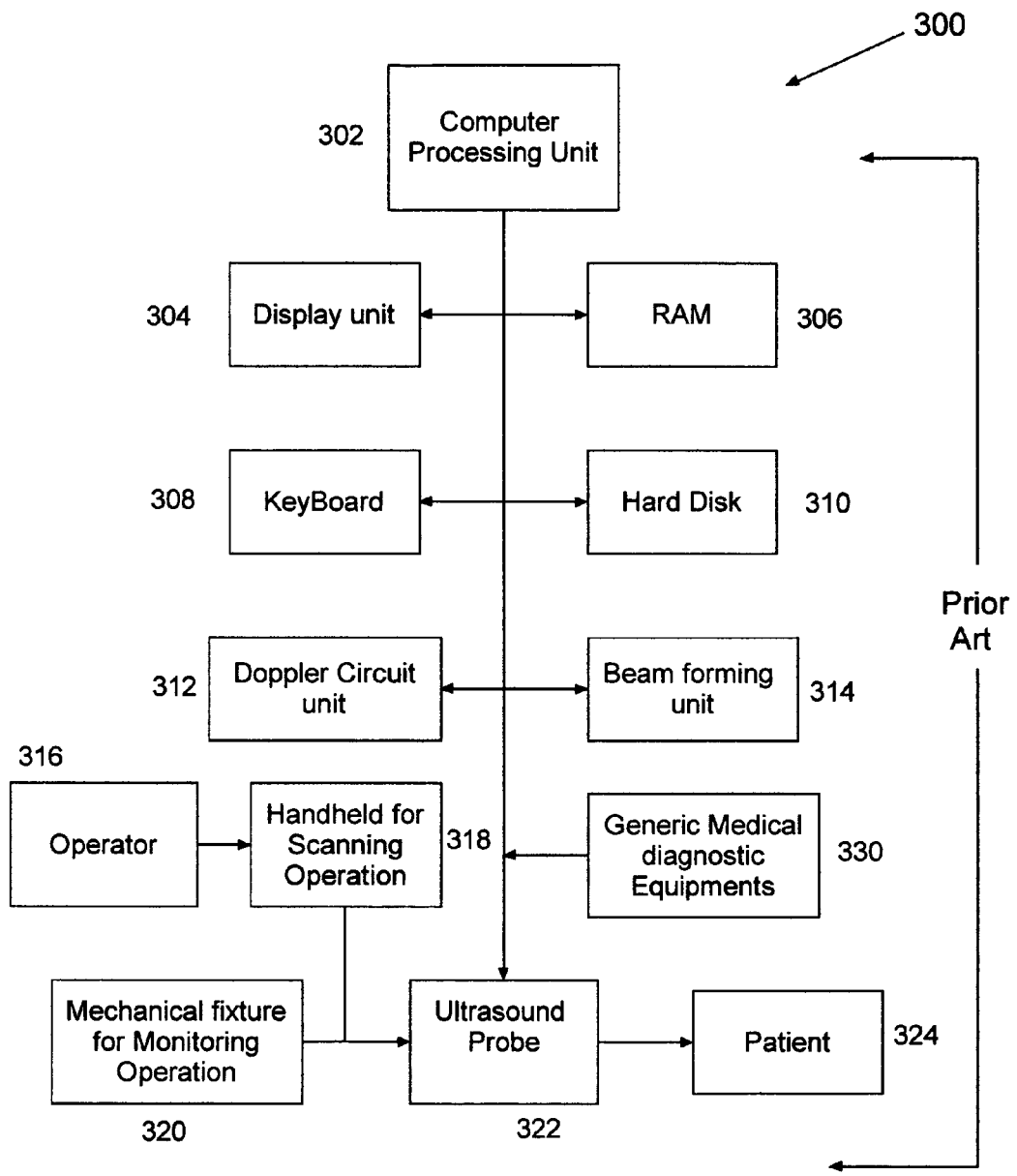

Currently, the conventional method of prior art ultrasound scanning system in FIG. 17 is through the repetitive transmission and reception of focused beams in one direction at a time, thereby building an image of accumulated consecutive scan lines from the received echoes, or Doppler. By manually pointing the line of cursor into the region of interest inside the image, a waveform of the pulsed Doppler (PW) or the continuous wave Doppler (CW) may be obtained [B].

As for the non-conventional method of ultrasound scanning, imaging techniques such as Synthetic Transmit Aperture [C], or STA, transmit unfocused beams into the image area to acquire data. The received echoes are then recorded by using all elements presented or a group of the elements in the Receive Aperture to generate a corresponding image. One reason a professional might choose the non-conventional STA method over the conventional method of imaging is the higher frame rate the non-conventional method provides and the lower amount of ultrasound energy required for scanning.

It can be used to calculate the blood flow velocity through the use of cross-correlation of images. Both these methods are feasible to be used with the proposed embodiment of the invention.

Figure 4:
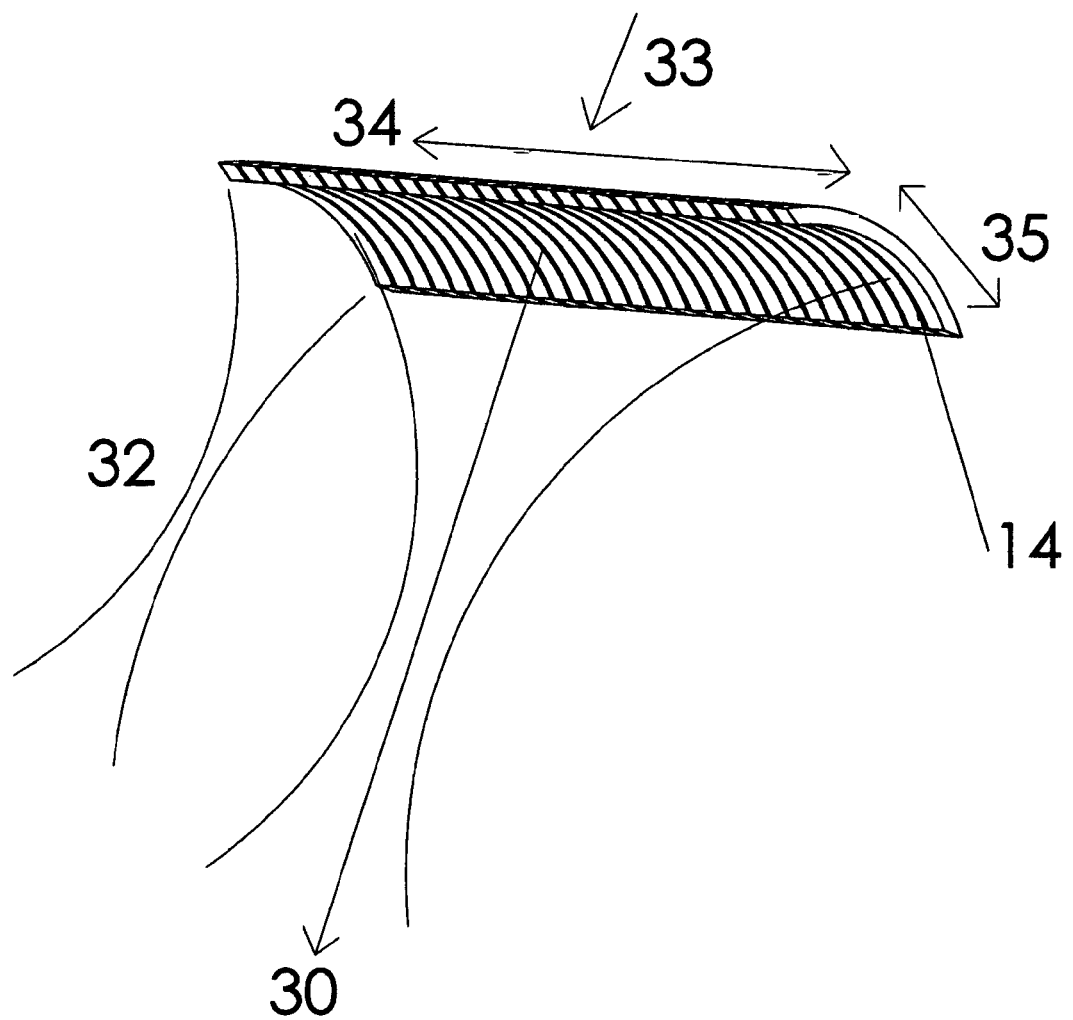

The transducer array of the proposed embodiment of the invention can be a phased array, where the element width would be equal or less than half of the wavelength of the ultrasound. The reason for using a phased array would be that it has the capability of deflecting larger angles to cover a larger field of view. To ensure that the elements transmit the ultrasound beams emitted in front of the transducer sequentially (as shown in FIG. 4), the elements of the phased array transducer are excited individually by the system. Then, the combination of all individual ultrasound waves from each element collectively form a wave front, which travels at the focal position designated and controlled by the system. The deflecting angle at which the wave front travels from the transducer array may thus be controlled by the degree of delay time among the varied elements.

If the embodiment of the invention uses a linear array, or curved linear array, to scan with the ultrasound beam, then the element width would be greater than half of the wavelength of the ultrasound, as compared to being equal or less than half of the wavelength of the ultrasound in the phased array previously mentioned. Generally, the precise deflecting angle used is dependant on the width of the transducer element, which in turn may be adjusted to suit the type of application required. Some applications may require a larger region to be covered by the ultrasound beam while others less. In the linear array, the deflecting angle is less than that of the phased array. However, in the instance of the curved linear array transducer, it can transmit ultrasound beams in different directions based on the curvature of the transducer. In the linear array, the position of the ultrasound beam can be changed simply by shifting the beam along the elements in the array.

One alternative embodiment of the proposed invention is to curve the PZT or PZN ceramic assembles, as diagramed in FIG. 4. By making the ultrasound beam, denoted by numeral 30, narrower in direction and orthogonal to the plane of scanning denoted by numeral 34, a higher strength of Doppler signals or sensitivity can be obtained. When the PZT or PZN ceramic assemblies are curved toward the direction perpendicular to the scanning plane, a focusing effect as denoted by numeral 32 will be achieved. By doing so, the ultrasound beam can be focused with higher intensity into the region of interest, such as the blood vessel in front of the transducer, which mechanically speaking, is in the out-of-plane direction 35 (meaning perpendicular to the scanning plane). The other benefit of the curvature is the increase in signal strength of the ultrasound in the transmitting and receiving modes. The transducer face 14 can be comprised of a focusing lens that can be made of RTV material and curved precisely to achieve the desired focusing effect. The RTV lens can be made very thin (less than 1 mm) and has the capability of attenuating ultrasounds up to 10 dB for the round trip of the transmitting and receiving mode. In consideration of the many benefits of this embodiment, the curved ceramic approach is therefore preferable.

As FIG. 3 delineates, the transducer array of the piezo-electric material faces the blood vessel. The transducer array will further be constructed to slant at an angle to the blood vessel of the patient so that the Doppler signal or Doppler shift frequency $f_d$ can be detected. Two Doppler shifts will occur: the first when the ultrasound beam has made contact with the patient's blood flow and again when the beam is reflected back. The Doppler equation is as follows:

$$f_d = \frac{2FV}{C}\cos\theta \quad \text{EQUATION 2}$$

where V is the velocity of the movement of the blood cells
F is the transmitted frequency
C is the ultrasound velocity
θ is the angle between the direction of the ultrasound beam 30 and the direction of blood flow According to the above Doppler EQUATION 2, if the given blood vessel is parallel with the surface of the patient's skin, such as a carotid artery set in the x-direction, the ultrasound beam 30 would be subject to an angle θ to the direction of blood flow.

Figure 5A:
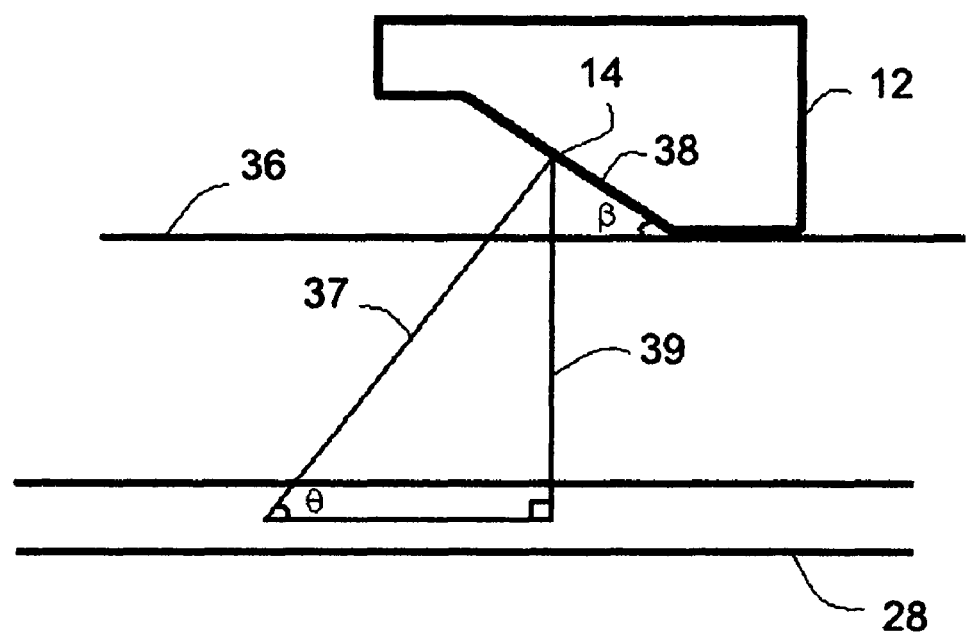

FIG. 5A illustrates an embodiment where the angle β is approximately forty degrees (40°), which is an angle between the transducer front face 14 and the skin of the patient. (Note, however, that any angle between zero degrees (0°) and ninety degrees (90°) may be used, depending on the orientation and location of the blood vessel relative to the transducer.) FIG. 5A further illustrates the corresponding geometry and the orientation of the blood vessel relative to the skin. The transducer array, subject to angle β, is relative to the surface of the patient's skin and is fixed at a predetermined angle for transmitting the best possible signal. The geometric relation between β and θ in FIG. 5A is given by the following condition:

$$\beta = 90° - \theta \quad \text{EQUATION 3}$$

Referring to FIG. 5A there is shown a transducer 12 with an array of transducer elements having the length of 2r (where r denoted by numeral 38) disposed outside a patient or subject's body with one end of the elements proximal to or in contact with the skin 36 at an angle β with respect to the skin 36. The center of a blood vessel 28 running parallel to the skin is shown with the transducer array 12 essentially positioned directly above it. The blood vessel is located at a height h, denoted by numeral 39, directly below the center of the array elements 14. The distance b, denoted by numeral 37, is the directed distance perpendicular the array from the center of the transducer element 14 to the center of blood vessel 28. Its direction toward the blood vessel 28 is also the same as the ultrasound beam 30 generated by the transducer. Therefore, the angle θ is the same as those indicated by the equations 2 and 3. In reference to the geometric diagram in FIG. 5A, b 37 can be obtained by the following the relations between θ and r 38 which is half of the length of the transducer array element, and h 39 the depth of the blood vessel.

$$b = \frac{(r\cos\theta + h)}{\sin\theta} \quad \text{EQUATION 4}$$

To obtain the optimized angle β for the best Doppler signal while maintaining the minimum distance between the blood vessel and the transducer, the following EQUATION 5 can be used to calculate this data:

$$M = \frac{f_d^2}{b^2} = \frac{\left(\frac{2FV}{C}\cos\theta\right)^2}{b^2} \quad \text{EQUATION 5}$$

where M is the merit value for which the maximum value would be the optimized condition that will provide the best signal for blood flow parameters.

To determine the maximum M as denoted by EQUATION 5 for the varying values of r and h the optimized angles β and θ can then be determined, as given in the following TABLE A:

TABLE A

| r (mm) | h (mm) | Optimized θ (degrees) | Optimized β (degrees) | Comment |
|---|---|---|---|---|
| 5 | 5 | 52 | 38 | |
| 5 | 10 | 49 | 41 | |
| 5 | 15 | 48 | 42 | |
| 10 | 5 | 56 | 34 | |
| 10 | 10 | 52 | 38 | |
| 10 | 20 | 49 | 41 | |
| 10 | 30 | 48 | 42 | |
| 10 | 40 | 48 | 42 | |

Figure 6:
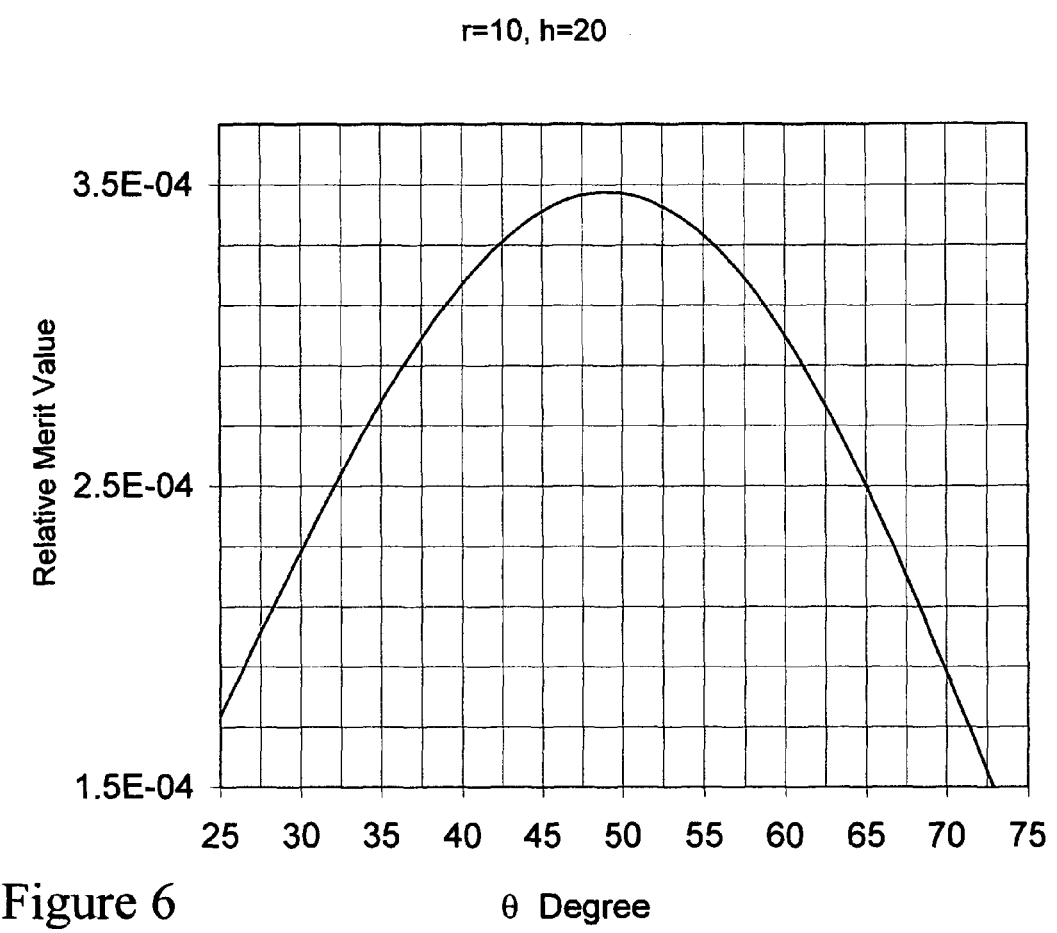

FIG. 6 further elucidates the optimized design of the invention regarding angle β. The graph shows the relationship between the merit value (M) and angle θ for an r at ten millimeters (10 mm) and h at twenty millimeters (20 mm). The reason for setting the values as such is because the values represent typical design parameters in the application of this invention for monitoring blood flow in a carotid artery. As illustrated, the maximum value of M in FIG. 6 occurs when θ is at forty-nine degrees (49°) and the β, as calculated from EQUATION 3, is forty-one degrees (41°). Therefore, the referenced equations and figures demonstrate that for the optimized design of this invention in such application, β, the angle of the transducer array in relation to the skin's surface, should be set at 41 degrees (41°)

Figure 5B:
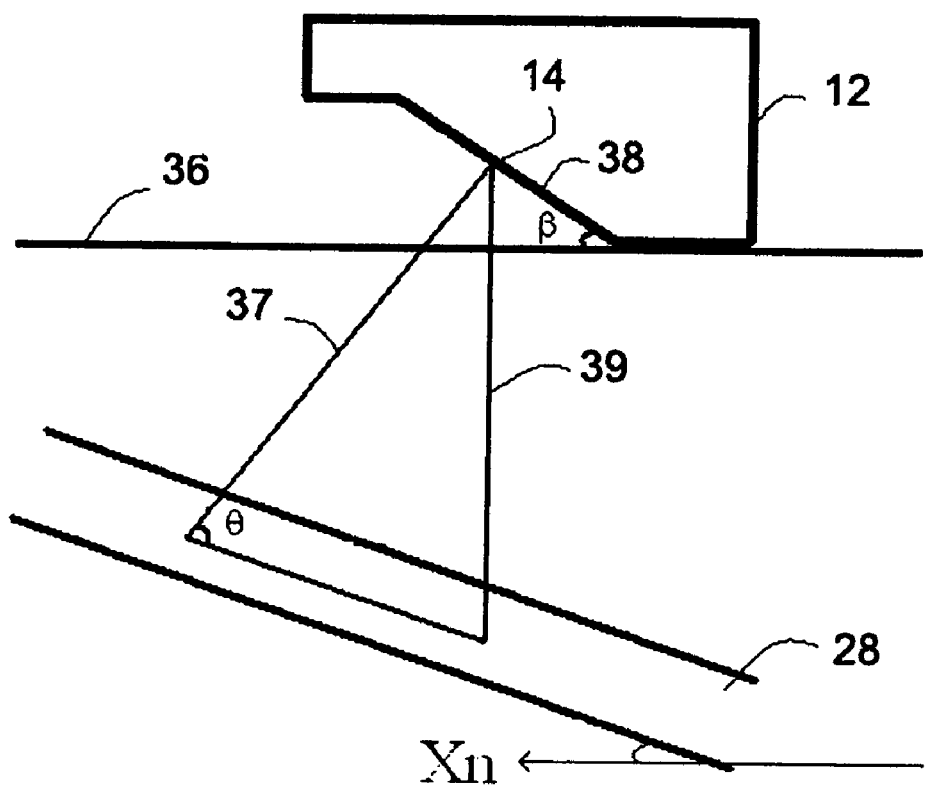

FIG. 5B shows a more general approach to the case where the blood vessel 28 has an elevation angle γ, between the reference line Xn that is parallel to the skin 36. For illustration of application on the arms and legs using the present invention, the blood vessel can have an elevation angle γ relative to the skin. In reference to the geometric diagram in FIG. 5B, the transducer array, subject to angle β, is relative to the surface of the patient's skin and is fixed at a predetermined angle for transmitting the best possible signal. The geometric relation between β, θ and γ in FIG. 5B is given by the following condition:

$$\beta = 90° - \theta + \gamma \quad \text{EQUATION 3b}$$

The corresponding b 37 as shown in FIG. 5B can be obtained by the following relations between θ and r 38 which is half of the length of the transducer array element, and h 39 the depth of the blood vessel.

$$b = \frac{(r\cos(\theta - \gamma) + h)\cos\gamma}{\sin\theta} \quad \text{EQUATION 4b}$$

Similar optimization method of using EQUATION 5 can be used to find the best optimized designed angle β of the transducer array with respect to the skin. In the particular case where γ=0° (blood vessel is parallel to skin), EQUATION 3b and EQUATION 4b is reduced back to EQUATION 3a and EQUATION 4a respectively.

Figure 7:
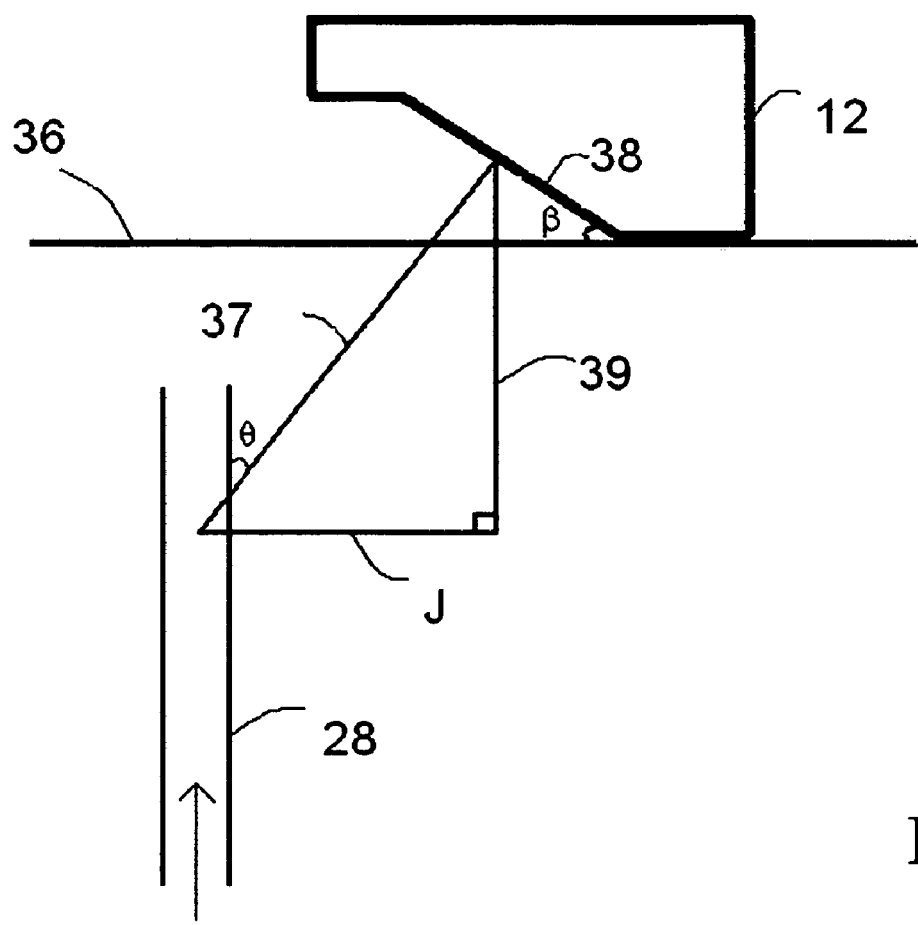
FIG. 7—Geometrical view of transducer array assembly with respect to blood vessel flowing toward skin FIG. 8—Graph of angle θ (x-coordinate) to relative merit value (y-coordinate)

In reference to EQUATION 2, the angle θ equal to 0 giving rise to cosine θ equal to 1 and the Doppler shift frequency is at maximum. In this instance, the ultrasound beam would be directly aligned with the direction of the blood flow. However, such a construction of the transducer would only be suitable for applications where blood in the vessel is flowing toward the surface of the patient's skin. FIG. 7 illustrates a middle cerebral artery (MCA), denoted by numeral 28, where the blood is flowing toward the transducer, denoted by numeral 12. Recall that in FIG. 5A, the diagramed blood vessel is parallel to the surface of the skin. Note that in FIG. 7, the blood vessel has been rotated ninety degrees (90°) and is thus perpendicular to the skin's surface. In reference to the geometric diagram in FIG. 7, the relation between θ and β is given by EQUATION 6

$$\beta = \theta$$

b 37 can be obtained by the following the relations between θ and r 38 which is half of the length of the transducer array element, and h 39 the depth of the blood vessel where ultrasound beams intercepted.

$$b_v = \frac{(r\sin\theta + h_v)}{\cos\theta} = J\sin\theta \quad \text{EQUATION 7}$$

where J is the horizontal distance (parallel to the skin) between the blood vessel and the center of the transducer array In this case, EQUATION 8 gives the relative Merit value:

$$M_v = \frac{f_d^2}{b_v^2} = \frac{\left(\frac{2FV}{C}\cos\theta\right)^2}{b_v^2} \quad \text{(EQUATION 8)}$$

Figure 8:
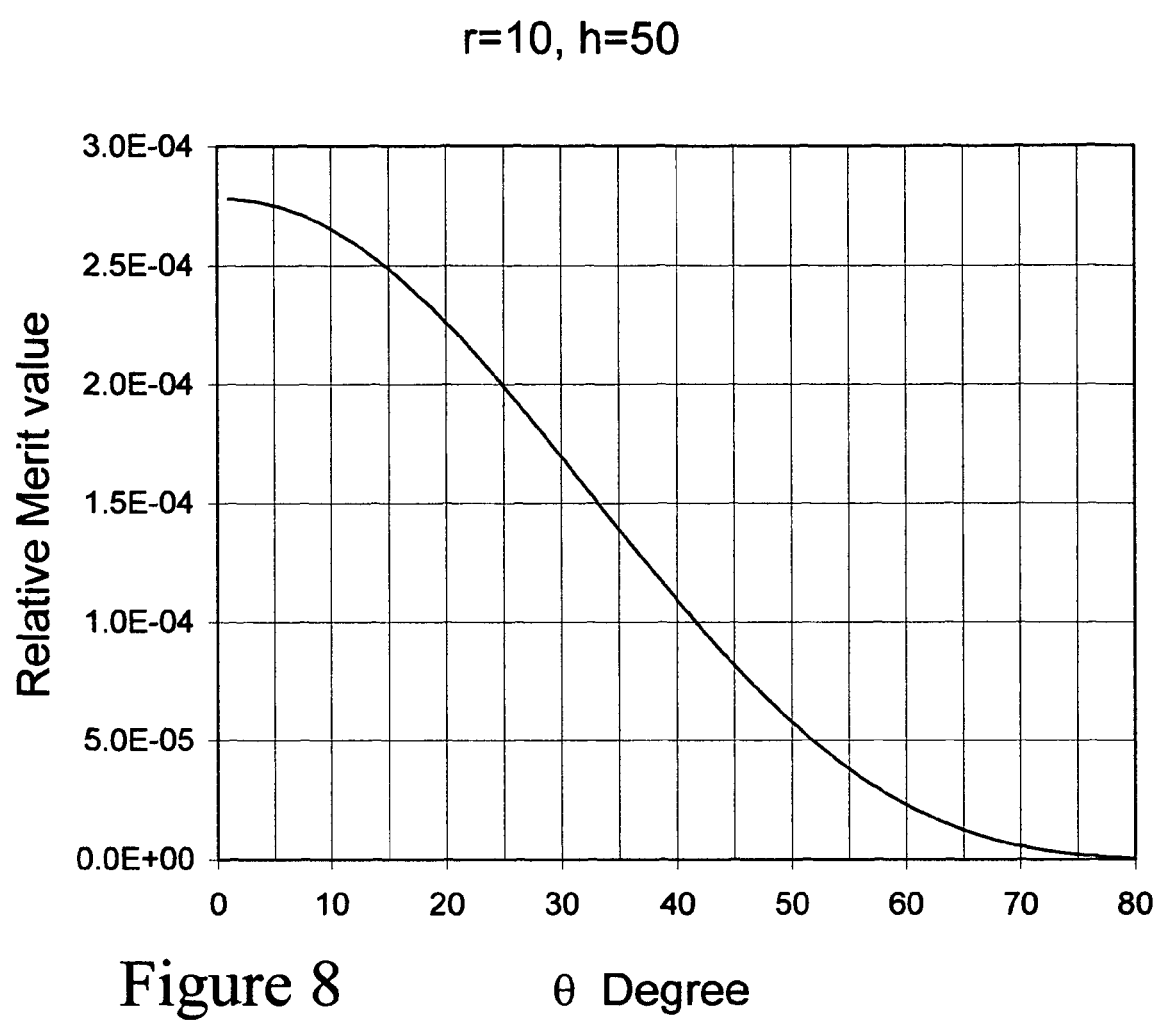

FIG. 8 further explicates on the correlation between M and angle θ. Note in the figure how the maximum value of $M_v$ occurs when θ is equal to zero degrees (020). This is the position where the ultrasound beam will meet with the blood vessel. The transducer array is then set at zero degrees (β=0°) to the surface of the skin, as shown in FIG. 7, and is positioned directly above the blood vessel. In the instance where θ and β are small angle, such as 10°, the drop in $M_v$ is relatively small. Only when θ exceeds 25° that the change in $M_v$ drops more significantly, as shown in FIG. 8. The characteristic of θ will be used in such applications as more effective searches for blood vessels that are flowing toward the skin of the patient. This application will be further delineated in another embodiment of the invention.

Figure 9:
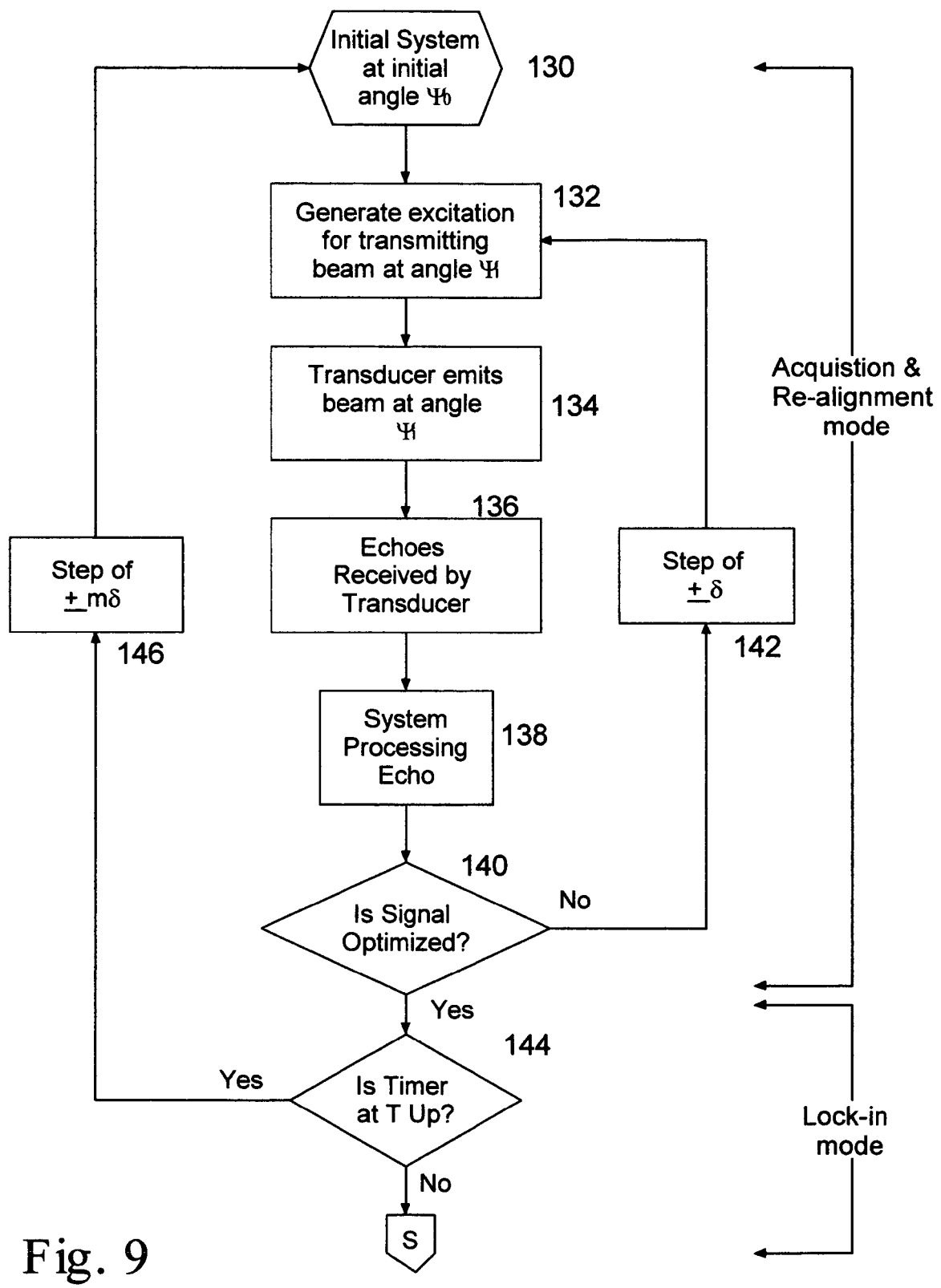
FIG. 9—Functional block diagram of an ultrasonic monitoring system with automatic re-alignment for blood flow measurement FIG. 10A—Functional block diagram of a system to display/record the trend of blood flow condition in accordance with present invention FIG. 10B—Graph displaying the normal trend FIG. 10C—Graph displaying the abnormal trend FIG. 11—Schematic diagram of two of the transducers to monitor the blood flow velocities of the left and right carotid arteries in accordance with the present invention FIG. 12—Top view of the brain with transducer of this invention on the transtemporal window of the skull for the ultrasonic blood flow measurement of the middle cerebral artery (MCA)
Figure 10A:
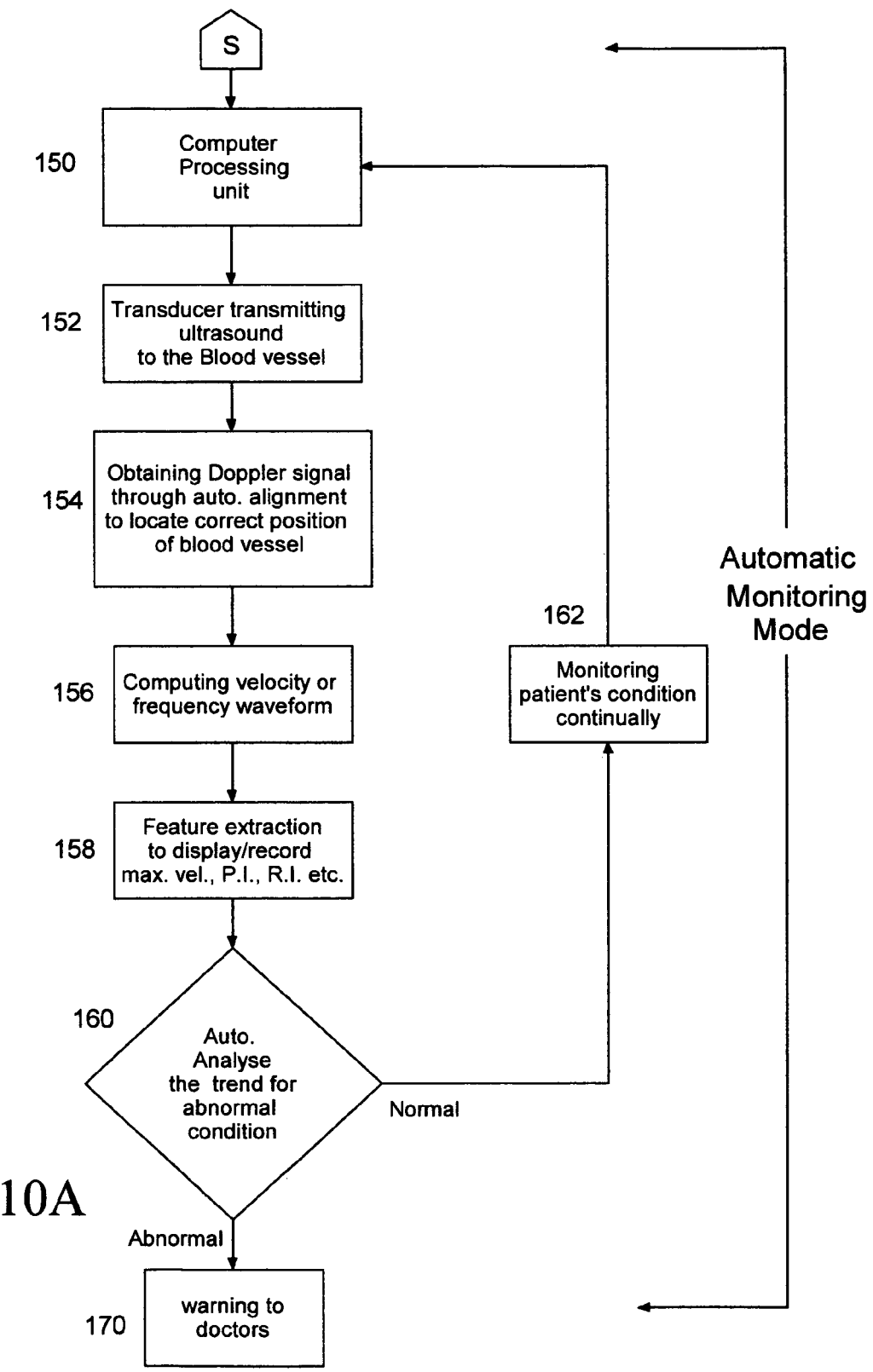

FIG. 9 is a flow chart outlining the methodology of how the proposed embodiment of the invention will detect the blood flow velocity and return feedback to control the deflecting angle such that the maximum Doppler signal may be obtained. The blood flow velocity is obtained once the Doppler signal has been analyzed by the system. The direction at which the ultrasound beam is emitted from the system is in close range to the initial angle $\psi_o$, or the angle that gives the maximum velocity. The initial angle can be initially determined manually when the proposed embodiment of the invention is attached to the surface of the patient's skin. The adjacent beams are deflected by a stepping angle δ, emitted around the initial angle $\psi_o$. δ can range from a fraction of a degree to a few degrees (δ), depending on the body type of the patient, the location of the blood vessel and the patient's movement conditions. Subsequent beams at different angle $\psi_i$, $\psi_{i+1}$, $\psi_{i+n}$ can further be emitted at slightly increased angle (n* δ) to search for the maximum blood flow velocity within the same cardiac cycle. The maximum deflected angle $\psi_{max}$ that the ultrasound beams can be deflected is related with the directivity angle given by EQUATION 1.

Typically, the maximum blood flow velocity occurs near the center of a blood vessel. The velocity gradually decreases the closer to the wall the blood flows. Meanwhile, the velocity of the blood flow outside the blood vessel is zero. As shown in FIG. 3, ultrasound beams are deflected in a two-dimensional plane subject to an angle θ to the blood vessel. Thus, the beams will cut across the one-dimensional blood flow in the vessel when the transducer assembly is positioned correctly into the region of interest.

The proposed embodiment of the invention searches and locates the maximum blood flow velocity by scanning the area of the vessel and locking into the corresponding angle at which maximum blood flow velocity occurs. Blood flow velocities to the left and to the right of the initial angle (the angle at which maximum blood flow velocity occurs) has less velocity at the respective angles $\psi_i$. This trend remains consistent even as the deflecting angles increase (such as $\psi_i$, $\psi_{i+1}$, $\psi_{i+n}$) and will continue to the wall of the blood vessel. Since the velocity outside the blood vessel is zero (0), the system will automatically stop searching at the corresponding angles outside the vessel. As the ultrasound beam scans around the adjacent positions to the original blood vessel, the maximum velocity is detected through comparisons of all detected velocities acquired by the scan. Then, the corresponding angle to the maximum blood flow velocity is locked into position and will continue to lock at the maximum velocity as shown in the acquisition and re-alignment mode in FIG. 9.

Thus, the initial angle is set and reset through the aforementioned process continuously during the cycle. The phased array transducer in one preferred embodiment of the invention is able to deflect the ultrasound beam up to +/− forty five degrees (45°). In the alternative preferred embodiment, the linear array transducer, with the larger element width, is able to deflect the ultrasound beam at smaller angles, as calculated from EQUATION 1. However, in the presently illustrated embodiment of the invention, the largest angles that need to be searched to detect the maximum blood flow velocity is less than +/− twenty degrees (20°), irrespective of potential spontaneous movements from the patient.

Alternate embodiments of the invention may be considered, offering different techniques incorporated for the purposes of enhancing detection speed, accuracy, and the signal to noise ratio of the ultrasound system. In an embodiment adopting the continuous wave Doppler system, ultrasound waves would be transmitted and received continuously. As shown in FIG. 4, one side of the dividing point 33 in the array 14 can be used for transmitted elements while the other side can be used for the received elements. However, it should be noted that the continuous wave (CW) Doppler system cannot detect the depth of the return echo from the blood vessel. In contrast, by using an embodiment of the invention adopting the pulse Doppler (PD) system, the system will automatically ignore irrelevant signals received by the transducer and will do so until a selected time interval after the pulse has been transmitted. When Doppler signals are to be collected, the receiver can then be switched on for the desired interval. The operator of the pulse Doppler embodiment can also define the range of the depth from which signals are to be collected around the blood vessel. Such a system can be further optimized by selecting the range of depth at which the signal should be searched at and thus improve the speed of detection. This option would be particularly useful in regions of the body where varying arteries and veins are in close proximity with one another. Accordingly, the unwanted blood flow information can be effectively eliminated and the accuracy improved.

To distinguish the precise direction of blood flow, whether it is moving toward or away from the transducer, the proposed embodiment of the invention would use the Quadrature Phase Detection technique. In the example of the monitoring of a carotid artery, such tracking of the correct artery is crucial for the patient's condition to be accurately monitored. If the system was to lack such a means of tracking, the carotid artery could in possibility be confused with one of the jugular veins. However, equipped with this means of tracking, the proposed system can then efficaciously detect the precise blood vessel in question (the carotid artery) since in the artery, blood flows from the heart to the brain and, in the vein, the brain to the heart. By detecting the direction of blood flow, possibilities of confusing blood vessels can be eradicated. Yet another method that could be utilized to accomplish the same effect is to employ Pattern Recognition. Through pattern recognition, arteries can be detected by their cylindrical shape through B-mode images from the ultrasound scan. By tracking arterial movement, the ultrasound beam can target the center section of the blood vessel through the acquired Doppler data.

The proposed embodiment of the invention is also equipped with a signal-to-noise improvement system. This may be accomplished through the proper focusing of an ultrasound beam (with an optimization of the beam profile) into the desired region. Where the width of the emitted beam is narrower, a stronger Doppler signal will offer a more intense ultrasound. Higher signal to noise ratios indicate that the effect of extraneous noise is relatively smaller. Thus, when the ultrasound beams are properly focused in both the scanning plane and along the out of plane direction, the signal to noise ratio will be increased such that extraneous noises from the environment and equipment will not affect the reading.

Figure 10B:
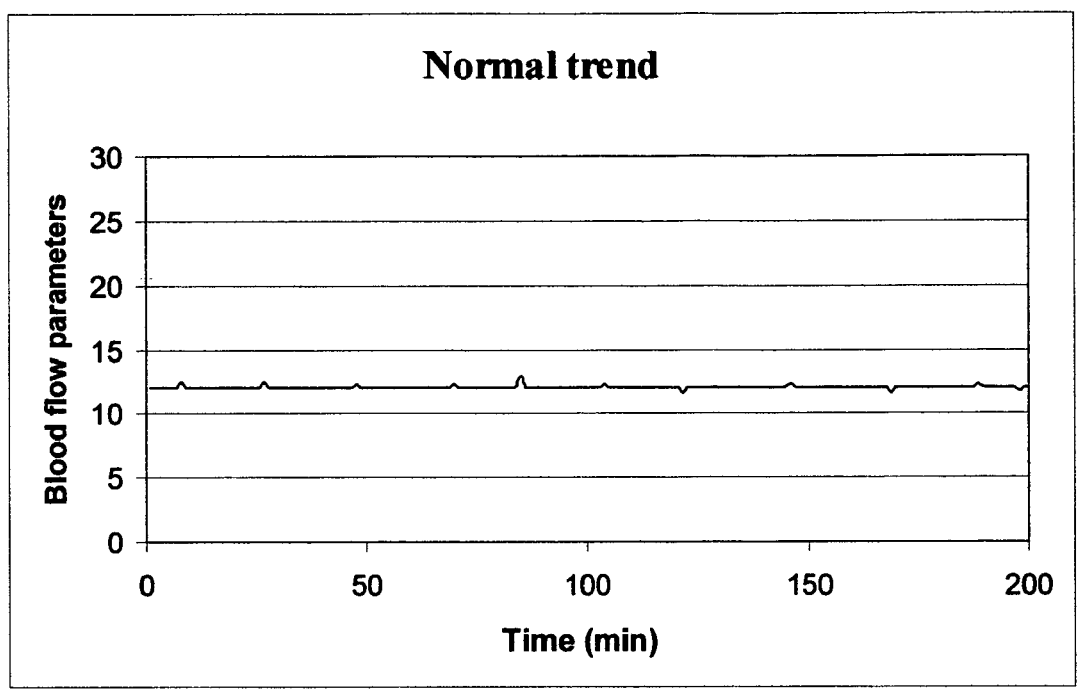
Figure 10C:
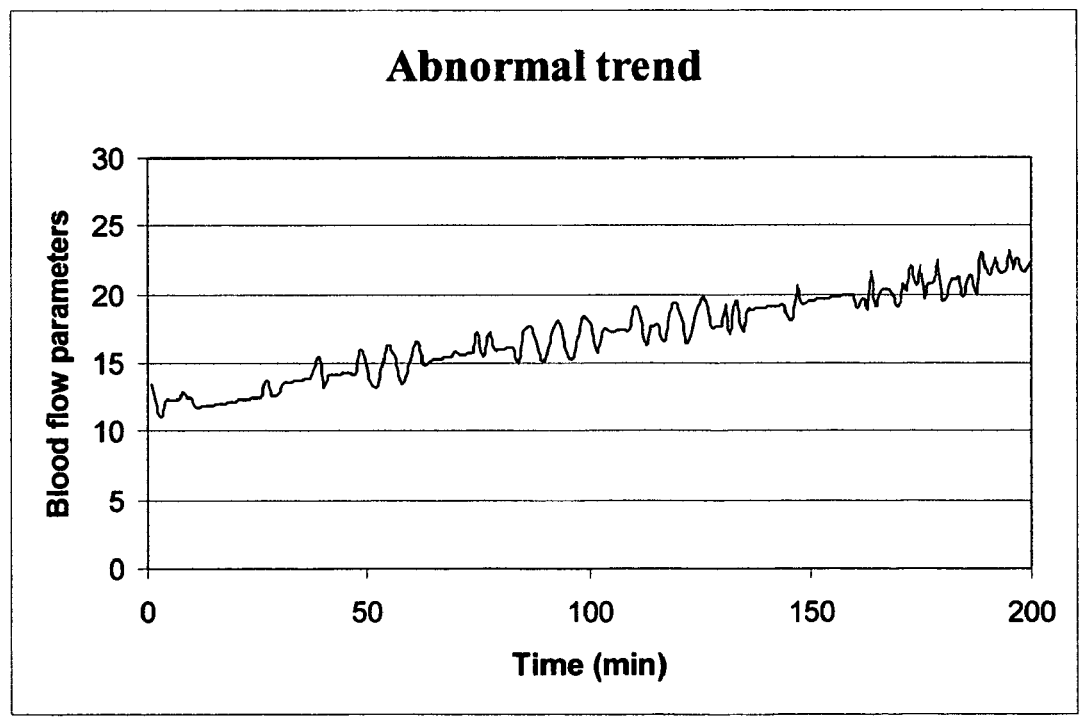

Ultrasound beams are to be sent from the transducer to the specified region in set time intervals for the lock-in of the maximum blood flow velocity. Time intervals (T) could thereby be adjusted and set depending on the blood flow parameters as shown in the Lock-in mode of FIG. 9 and the Automatic Monitoring Mode of FIG. 10A. After the initial Doppler signal has been locked in, signals will subsequently be sent out and the system will compare the recently received signals with the lock-in beam to update the maximum signal. If the system determines the Doppler signal of neighboring beams from the lock-in beam to be stronger, then the lock-in beam will change and its initial angle reset to the corresponding position for the updated stronger beam. The system will then deflect the beam continually in this lock-in position until the next interval of time (T) where the system will once again compare the neighboring beams to identify the new maximum signal. The exact interval of time (T) at which the system is to operate on may be adjusted according to the trends recorded by the Doppler signal. For example, when the change in Doppler strength is minimal, T can be greater, meaning the interval of time longer. Then when the system detects an increasing or decreasing trend in Doppler strength, T can be shortened so that more Doppler information will be obtained over the monitoring period. The blood flow parameters as noted in FIG. 10B and FIG. 10C include the following: maximum blood flow velocity, peak systolic velocity, mean peak velocity, time average velocity, pulsatility index (P.I.) and resistance index (R.I.). Such parameters are necessary information for a medical professional to obtain in order to properly monitor a patient's condition during or after a surgical procedure.

The pulsatility index, or P.I., summarizes the degree of pulse-wave damping at the arterial sites. In this manner, the P.I. is therefore directly related to blood flow conditions. Physiological and pathological changes in the patient can be reflected in the trends displayed by this index where the lower the P.I., the greater the degree of damping. A stenosis in the blood vessel (the constriction of a passageway or opening in the body) will lead to a reduced P.I. at points proximal to the stenosis. The resistance index, or R.I., is a common index supplement to the P.I. that can be used to detect changes in pathological conditions in the patient. Moreover, the R.I. indicates the degree of resistance to the blood flow in distal circulation. A stenosis in the blood vessel potentially leads to reduced blood flow, thereby increasing the resistance. A high resistance index can also be a sign of decreased flow in the capillary system, as generally found in diabetic patients.

A patient's cardiac conditions can be readily monitored by the proposed invention. Such cardiac conditions are measured through the system's observation of blood flow parameters. A flat display of the parameters indicates to the operator of the device of this invention that the patient's condition is relatively unchanged through the monitoring cycle (See graph titled "Normal Trend," in FIG. 10B). On the other hand, a gradual increase over time, where the blood flow parameters oscillate, indicates changes in the cardiac condition (See graph titled "Abnormal Trend," in FIG. 10C). In such instances of an abnormal trend, a warning to the physician may be issued and proper treatment administered to the patient. This could make a significant difference by preventing further deterioration of the patient's condition that could otherwise have gone undetected.

Figure 11:
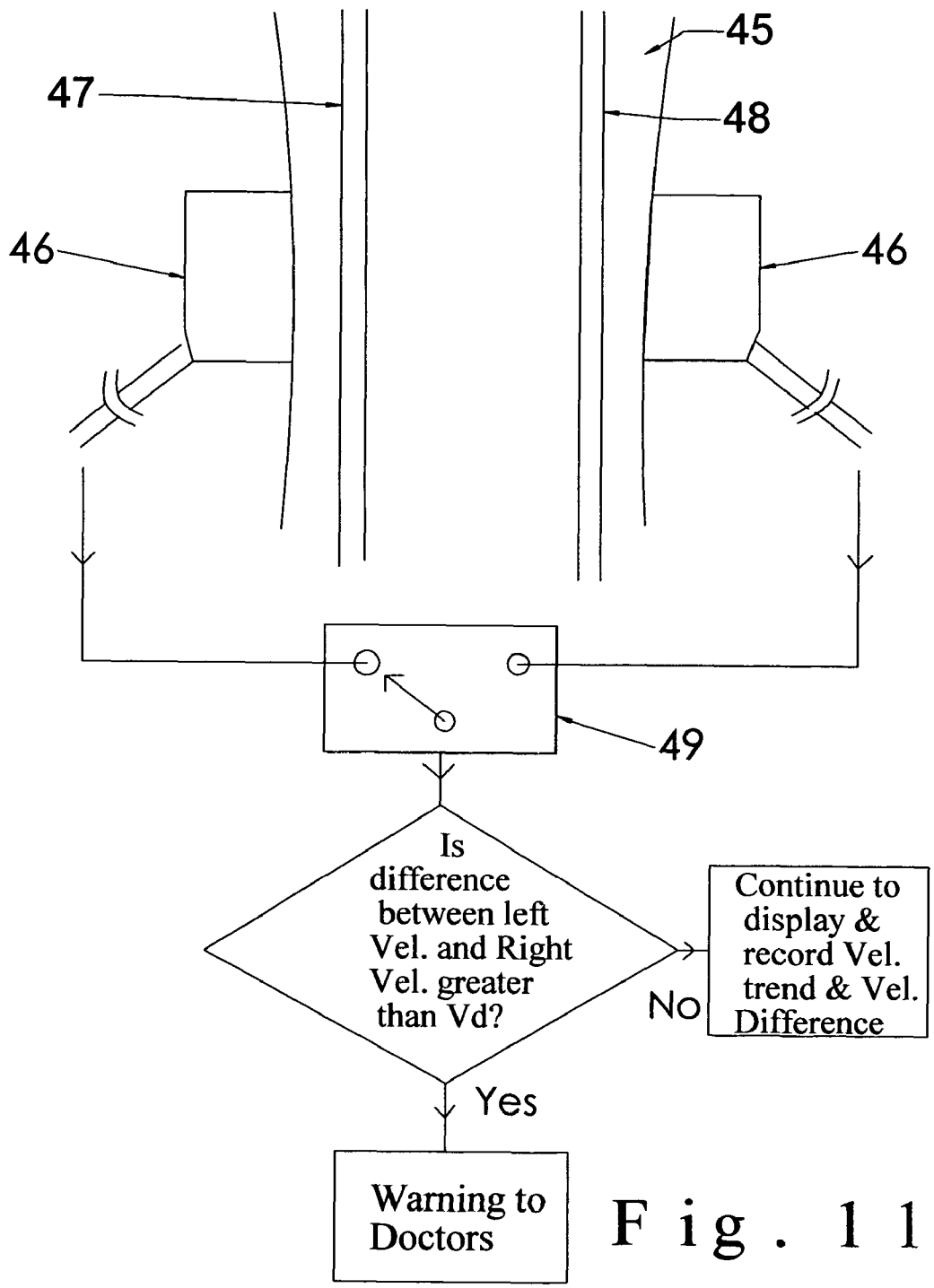

One of the main applications for the ultrasound monitor is the monitoring trends in blood flow velocity through the carotid artery to the brain. By using two of the transducers of present invention, one on the left side of carotid artery 47 and one on the right side of the carotid artery 48 in the neck 45, the difference of velocities between the two arteries can also be obtained as shown in FIG. 11. There is an electronic switch 49 which can connect the ultrasound system to either one of the monitors over a period of time (for example, anywhere from 1 cardiac cycle to few cardiac cycles or a preset time period which can be between 1 second to 10 second) alternatively. The trend of each side of the blood flow monitor can be recorded and compared by the computer of the ultrasound system. Under normal condition, the peak velocity and other blood flow parameters of the blood flow through the carotid arteries between the left side and right side to the brain should be close to each other. When the difference between the left velocity and right velocity has a marked difference, it indicates there could be problems in the patient including stokes or heart attack. A predetermined reference Vd for the difference in velocities can be established by doctors and researchers to define the risk level of the patient. Then, if the difference between the velocity measured in the left 47 and right carotid arteries 48 is greater than the set Vd, the monitoring system will send a warning signal to physicians. Such early diagnosis of a patient's condition can prevent neuronal damage to the patient's brain.

The invention is further useful in the monitoring of intracranial vessels of the Circle of Williis by a transcranial Doppler, or TCD. For this application, a middle cerebral artery (MCA) would be selected, due to its common use for TCD monitoring applications in clinical and hospital environments. Additionally, the PMN ceramic material, or other high dielectric constant PZT material, with frequency levels from 1 MHz to 2 MHz would be used to achieve the best signal-to-noise ratio. This is to compensate for the strong attenuation of ultrasound signals in the skull.

Figure 12:
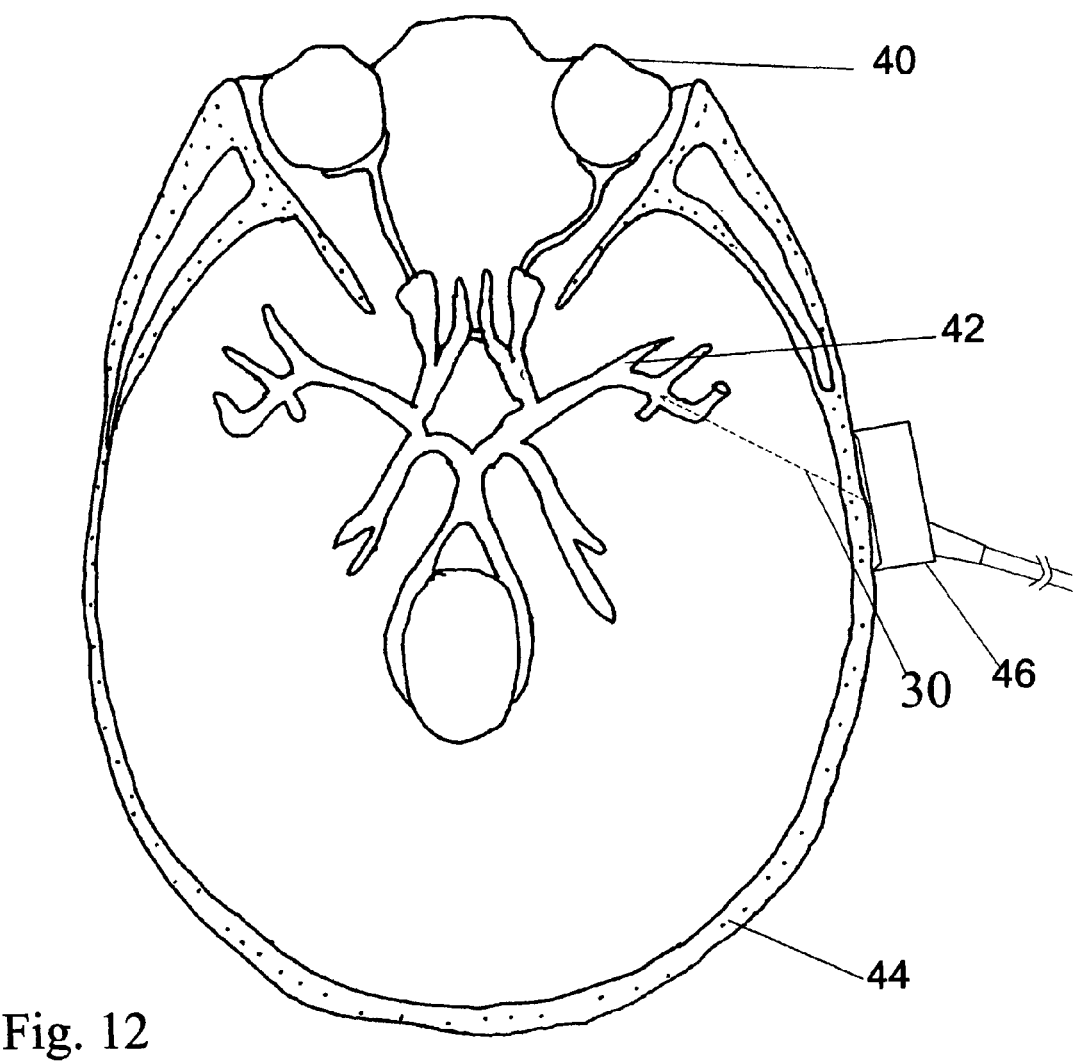
Figure 13:
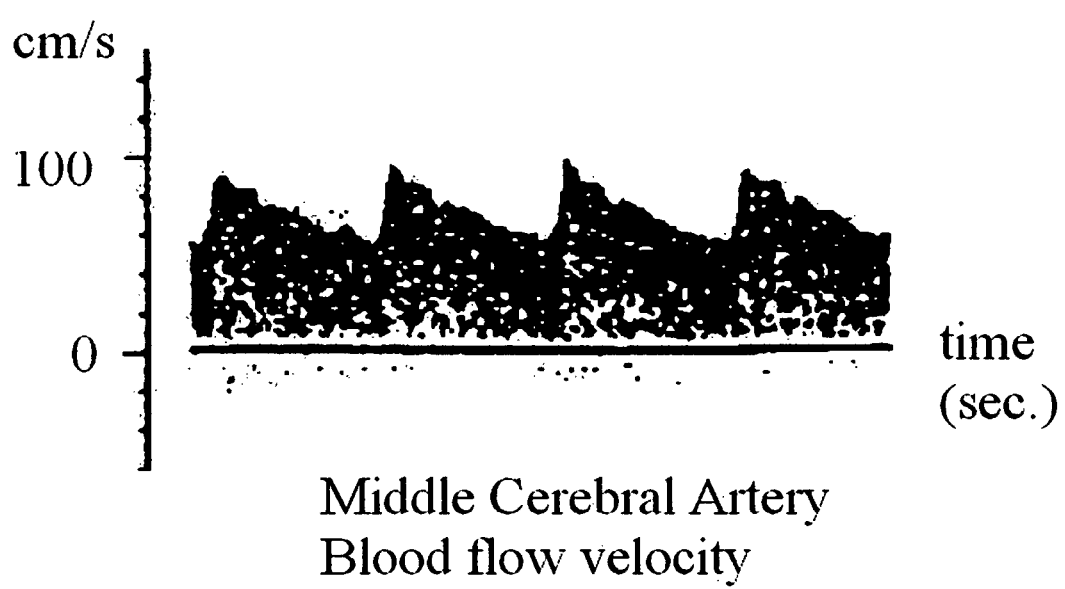
FIG. 13—Doppler waveform showing the blood flow velocity of the MCA in four cardiac cycles FIG. 14—Side view of the skull with transducer of this invention on the transtemporal window for the ultrasonic blood flow measurement of the middle cerebral artery (MCA)

In measuring the blood flow condition of MCA 42, the transducer array assembly, as denoted by numeral 46, is placed in the transtemporal window for TCD so that the transducer is perpendicular to the MCA 42 rather than parallel. Such is because the blood flow of the MCA 42 is toward the transtemporal area near the ears on both the left and right side of the brain, as illustrated in FIG. 12. A typical Doppler signal of the MCA 42 is shown in FIG. 13. This signal is easily missed by the existing commercial TCD transducer, which used only one to 2 PZT elements to transmit and receive the ultrasound beam. When the ultrasound beam is not cutting across the MCA 42, there will be no Doppler signal detected.

For the invention to measure the blood flow condition of MCA 42, the ultrasound beam will need to meet the MCA 42 inside the brain at a range gate (depth setting of the ultrasound beam) of around thirty millimeters (30 mm) to sixty millimeters (60 mm). Three major factors, as listed below, can ensure that the correct and optimized signal be obtained from the MCA 42:

First, the range gate set by the ultrasound system needs to be set between thirty millimeters (30 mm) to sixty millimeters (60 mm), as mentioned, to exclude miscellaneous and unwanted signals from other nearby blood vessels.

Figure 15:
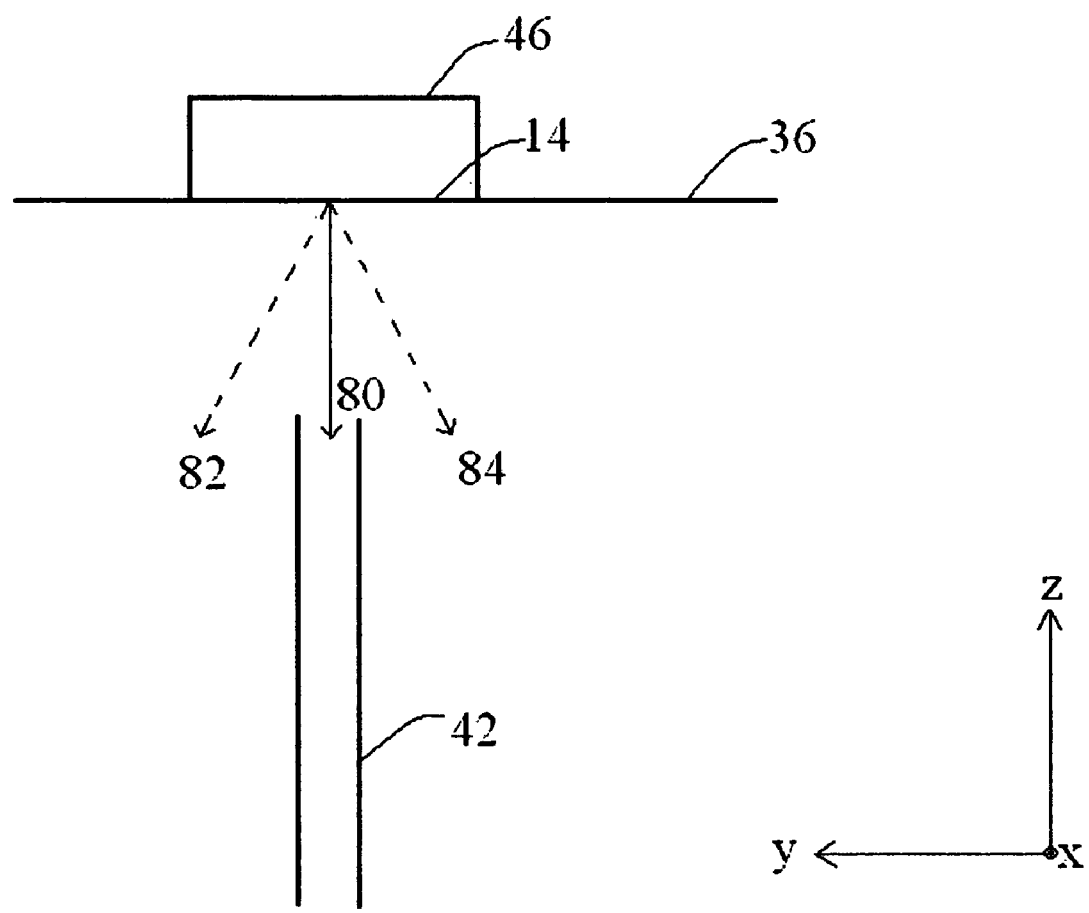
FIG. 15—Transducer directly above a blood vessel flowing toward the transducer, for example: MCA FIG. 16—Different position of transducer relative to MCA FIG. 17—Prior Art of existing commercial ultrasound system for diagnostic application or monitoring application FIG. 18—Incorporate present invention into existing platform of ultrasound system to become an automatic signal-optimizing monitoring system for blood flow measurement.

Second, the angle of the transducer array should be inclined at a predetermined angle $\beta$ (=$\theta$) relative to the surface of the skin, as illustrated in FIG. 7. The ultrasound beam will in turn cross the MCA 42, which is flowing toward the transducer at an angle $\theta$. In the embodiment of the invention, as illustrated in FIG. 7, the angle $\theta$ would range from zero degrees (0°) to twenty-five degrees (25°). As determined from EQUATION 8, the maximum signal with the largest Merit value (M) occurs when $\theta$ is at zero degrees (0°). The Merit value M fall off gradually until $\theta$ passes 25°, where M starts to drop in value more significantly as shown in FIG. 8. In a real-life application of the invention, spontaneous movements by the patient may temporarily cause the ultrasound beam 80 to swing slightly off the artery and result in a missed Doppler signal of the MCA 42, as illustrated in FIG. 15 ($\beta$=0°). But the automatic re-alignment technique of the proposed embodiment of the invention can recover the original signal when the slight movement is along the x-axis. This is due to the scanning plane 34 of the transducer is along the x-direction. However, when the slight movement of the transducer is in the y-direction, the automatic re-alignment technique may not able to get back the original Doppler signal as shown in the ultrasound beam 82 and 84. The transmission of ultrasound beams 82 and 84 are not cutting across the MCA 42 in this situation and the Doppler signals of the blood vessel are missed as shown in FIG. 15.

Figure 14:
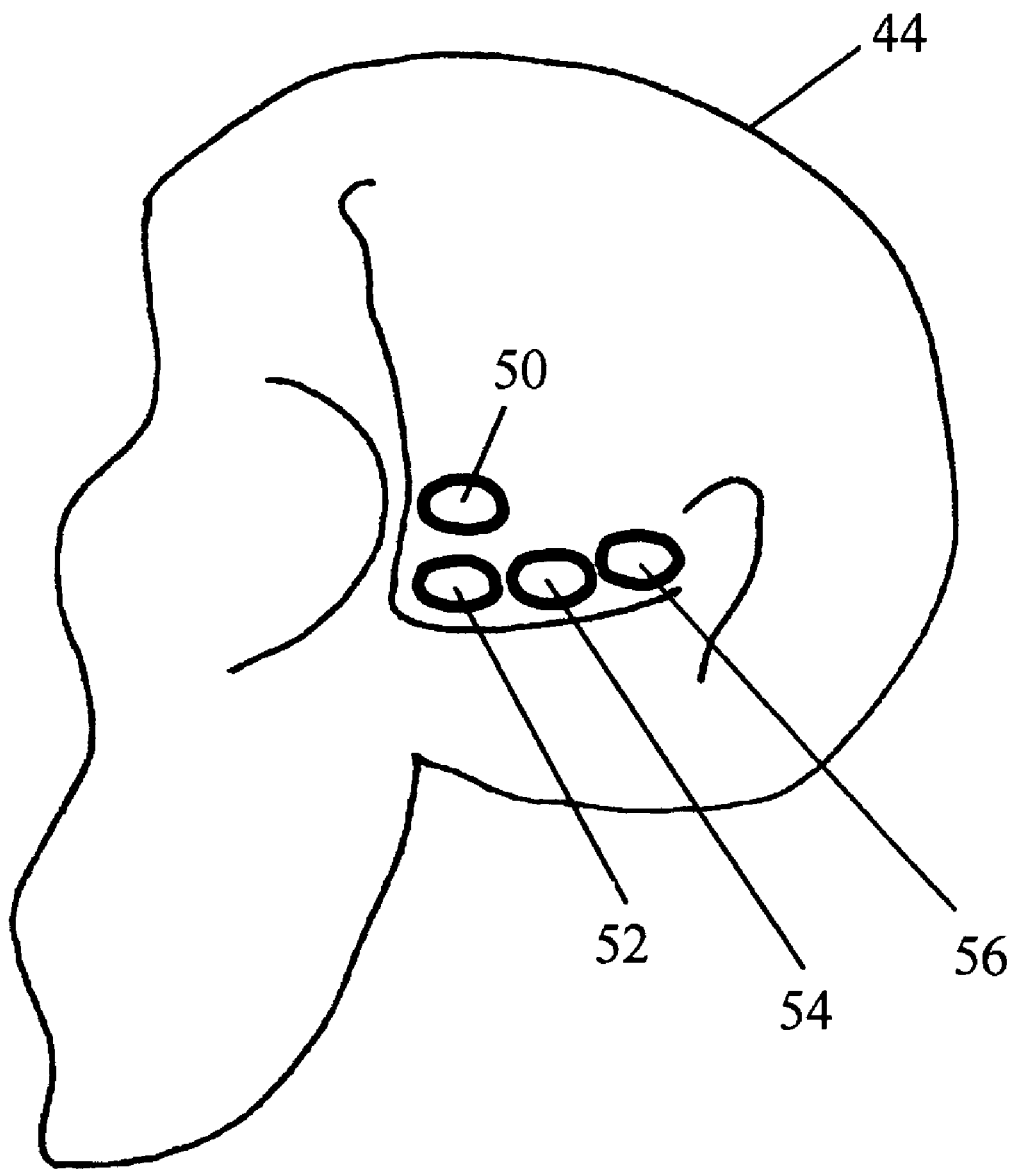
Figure 16:
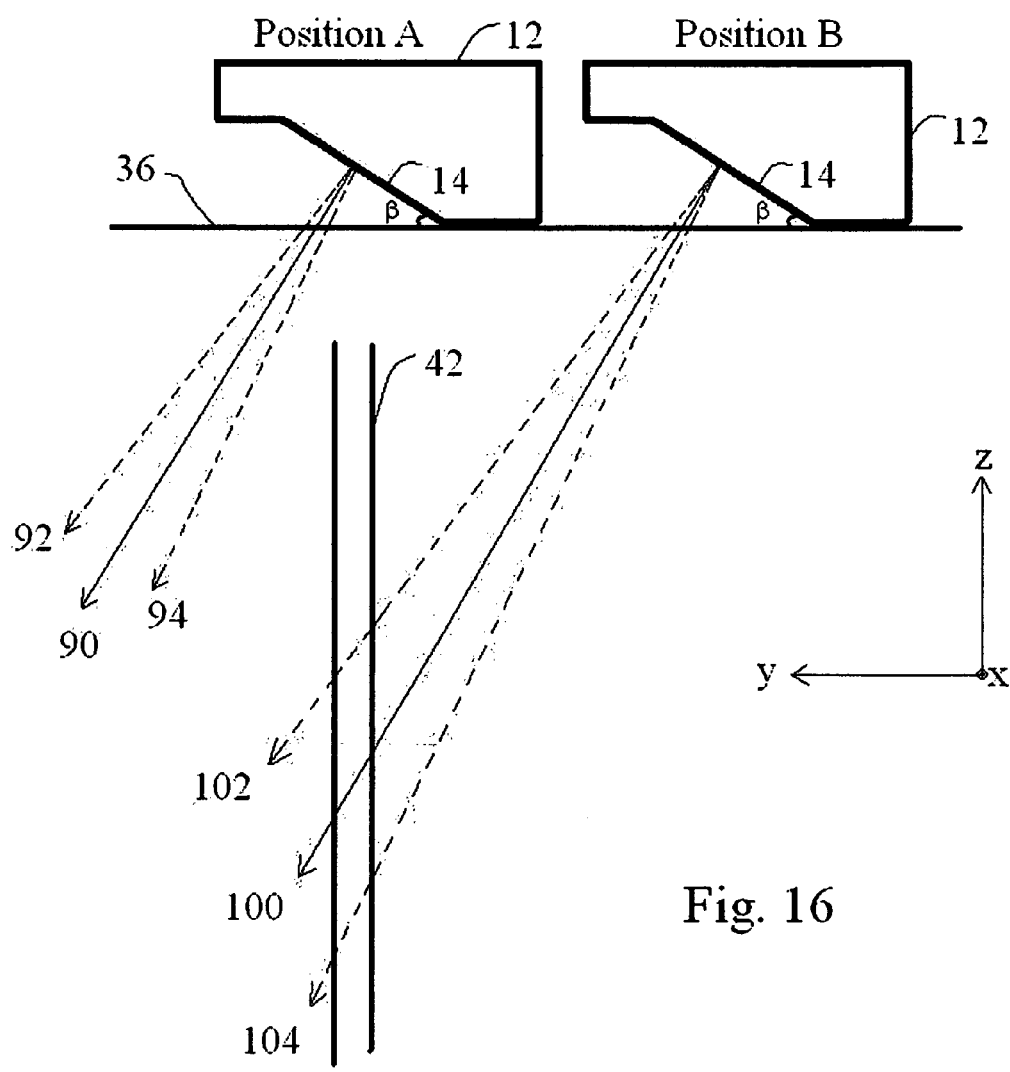

As shown in FIG. 16, when the transducer is in position B and the transducer array becomes subject to the small angle of $\beta$ (>0) relative to the skin's surface, the chance of the scanning plane meeting the MCA 42 is maximized. Even when there is slight transducer movement that would cause the scanning plane direction to shift from 100 to 102 or 104 (FIG. 16), the scanning plane can still cut across the MCA 42 and the transducer array to receive the Doppler signal of the blood flow. The transducer 12 can be placed in any location 50, 52, 54, or 56 to search for the optimized position as shown in FIG. 14. As long as the transducer 12 is in position B instead of A (FIG. 16), the Doppler signal can always be picked up by the transducer 12. When the transducer is placed in A position (FIG. 16), none of the ultrasound beams 90, 92 and 94 will cut across the MCA 42. In this case, the transducer need to be moved to another position selected from 50, 52, 54, or 56 so that position B can be maintained. As an illustration of this embodiment, the designed angle for $\beta$ is about 10 degrees for J=10 mm so that the distance from the transducer array to MCA is between 30 mm to 60 mm (EQUATION 7, EQUATION 8 and FIG. 8)

Lastly, the transducer may be configured to rotate around to search for the appropriate scanning plane so that the beam may be emitted across the MCA, as illustrated in Position B of FIG. 15. To operate this invention for the purpose of monitoring MCA of the brain, the following steps may be taken:

STEP 1: Consider the MCA 42 inside the brain to be likened to the inside of a black box, where only proximate locations are known. The blood flow direction of the MCA will thus be toward position 50, 52, 54, or 56 near the ear (FIG. 14).

STEP 2: The monitoring system is turned on. (Detection of the Doppler signal, or blood flow velocity, commences.)

STEP 3: The transducer array, denoted by numeral 46, with a design angle of β equal to approximately ten degrees (10°) is set by the monitoring system. (Note: Although the ten degrees is for the ordinary patient, any angle between zero and twenty-five degrees may be set according to the size and shape of the patient.)

STEP 4: The transducer array is then placed in the position denoted by 54 (See FIG. 14). The purpose of this is to search for the maximum Doppler signal. The array can slide into position 52 or position 56 for comparison. Then, selection of the best possible position (B) will provide the maximum Doppler signal. The Doppler signal can further be improved by rotating the transducer array in position B (FIG. 16).

STEP 5: After the optimized position and orientation of the transducer array is determined, the array can then rock slightly in different directions to simulate the patient's movements. The Doppler signals should still be detected as explained previously and the ultrasound beams' relative position should be like those in position B of FIG. 16.

STEP 6: The transducer can then be secured to the patient's skull, as denoted by numeral 44, in accordance to the techniques previously mentioned.

STEP 7: The rest of the operation of the ultrasound system will then be similar to those methods previously mentioned.

The proposed invention can also be applied to the measurement of flow-mediated dilation, or FMD. Presently, the conventional method of obtaining FMD information is through longitudinal ultrasonic scans of the brachial artery. By way of the proposed invention, the same FMD information can be obtained through transverse ultrasonic scans, as shown in FIG. 2. To calculate FMD, the following EQUATION 9 may be used:

$$FMD = \frac{(D2 - D1)}{D1} \times 100\% \quad \text{EQUATION 9}$$

where D2 is the diameter of the artery after the cuff release (reactive hyperemia)

D1 is the original baseline diameter

The transducer in the proposed embodiment of the invention is subject to angle θ with respect to the blood vessel. Thus, the measured diameters will have a factor of sign θ in the denominator. The FMD is a ratio of the change in diameters, thereby canceling out sin θ. Moreover, the calculation is independent of the angle θ, as show in the following EQUATION 10:

$$FMD = \frac{(D2/\sin\theta - D1/\sin\theta)}{(D1/\sin\theta)} \times 100\% \quad \text{EQUATION 10}$$
$$= \frac{(D2 - D1)}{D1} \times 100\%$$

Both D2 and D1 can be measured from the ultrasound images produced by this invention so that FMD ratio can then be calculated.

Yet another application of the invention is for the monitoring of graft blood flow conditions during dialysis. Low volume of blood flow through an access graft can confirm graft failure and other similar dysfunctions. Grafts that are at high risk for thrombosis can be detected through continual monitoring of blood flow velocity of the arterial graft. The transducer array assemblies, denoted by numeral 12, of this invention is compact enough to be placed on the arm or directly above the graft, which is approximately parallel to the patient's skin. The design configuration of the transducer array assembly 12 is diagramed as in FIG. 5.

Figure 18:
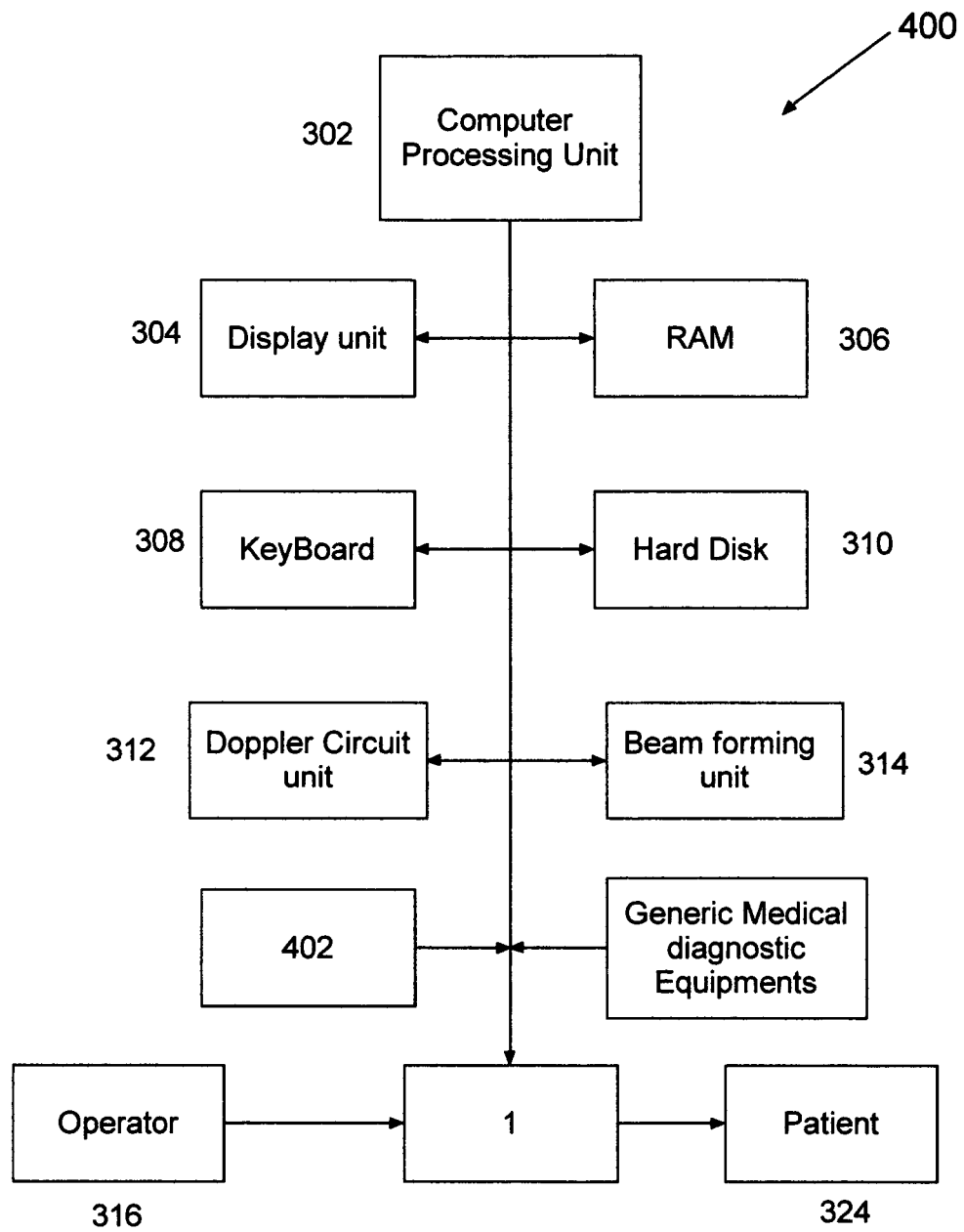

FIG. 17 shown the prior art ultrasound system with CPU 302, Display unit 304, RAM 306, Hard Disk 310, Doppler Circuit 312 and Generic Medical diagnostic Equipment(for example, interface with ECG unit) that the operator 316 use handheld transducer 318 for scanning operation to obtain images of the patient 324. In the case of existing monitoring operation 320, handheld transducer or mechanical fixture need to be used to obtain the Doppler signal of the patient 324. The present invention can be incorporated into the existing platform to become an automatic signal-optimizing monitoring system for blood flow measurement as shown in FIG. 18. An automatic signal-optimizing medical ultrasound measurement and monitoring system 1 using the transducer assembly described in this invention can be implemented by Software upgrade 402, which functions and steps presented in this invention.

Modifications, additions, and substitutions can be made to the invention changing it from the proposed embodiment and yet retain the spirit and scope of said invention. Those skilled in the art may further acknowledge that the advantages and benefits associated with the proposed embodiment of the invention can still be provided through other design configurations and processes. The invention is by no means limited to the particular disclosure above; rather the scope of the invention may be determined by the subsequent claims below.

I claim:

1. An auto-signal-optimizing transducer assembly configured for transmitting ultrasound to, and receiving ultrasound echo signals returned from, a blood vessel disposed in a patient's body region in which said blood vessel is oriented at a vessel elevation angle relative to the patient's skin surface, said auto-signal-optimizing transducer assembly comprising:

a) an ultrasound transducer component having a front face that transmits ultrasound along a scanning plane directed away from said face and receives ultrasound echo signals returned along said scanning plane;

b) signal connection means for coupling said transducer component to an ultrasound generator and processor unit that excites said transducer component to transmit said ultrasound and processes said returned ultrasound echo signals received by said transducer component;

c) securing means configured for detachably and repeatably holding said transducer component adjacent to said skin surface and oriented in azimuth adjacent to said body region and to hold said transducer component so said scanning plane is disposed at a fixed transducer elevation angle relative to the skin surface, and is oriented in azimuth on said skin surface to optimize initial returned echo signals from said blood vessel disposed at a vessel elevation angle relative to said skin surface, in which said securing means comprises:
d) a housing body fixedly encapsulating, protecting and holding said transducer component, said housing body comprising:
i) a top with spaced apart, parallel front and back edges extending between two spaced apart, parallel side walls
ii) longitudinal ribs extending along opposite parallel side walls;
iii) a perpendicular bottom face between the two opposite side walls presenting an opening for the ultrasound and received ultrasound signals to pass between said face of said transducer component and said skin surface when said housing body is adapted to secure to said body portion;
e) a housing body holder comprising:
i) a lateral base member;
ii) a rigid open rectangular channel with a back wall between two parallel side walls extending upright from said lateral base member, the holder side walls spaced apart to receive said housing body with said parallel side walls fitted closely within, the inside of the two holder side walls having opposing grooves formed to slidingly receive and retain said longitudinal ribs of said housing body when said housing body is fitted against said back wall of said channel;
iii) the lateral base member forming an opening co-extensive with said fitted housing opening;
iv) opposing, thin lateral wings having respective upper and lower surfaces, said wings extending away from said holder opening to distal free ends, said wings shaped to fit closely proximal on said skin surface portion when attached adjacent to said body region, and having sufficient strength to reliably maintain said holder and said housing body in a fixed position and orientation when attached to said skin surface portion;
f) housing holder attachment means configured to removably attaching said lateral wings to said skin surface portion.

2. The auto-signal-optimizing transducer as set forth in claim 1, wherein said ultrasound generator and processor unit is adapted to excite said transducer component to transmit said ultrasound as a beam sweeping over a range of deflection angle along said scanning plane and to process said returned ultrasound echo signals received by said transducer component.

3. The auto-signal-optimizing transducer assembly as set forth in claim 1, in wherein said fixed transducer elevation angle is fixed at an angle $\beta$ relative to said skin surface portion according to the relation $\beta=90°-\theta+\gamma$, where $\gamma$ is the elevation angle of said blood vessel relative to said skin surface portion and $\theta$ is the angle between the direction of the ultrasound beam and the direction of blood flow, wherein $\beta$ can be optimized by a relative Merit method based on the geometry of the transducer assembly, $\gamma$ and $\theta$.

4. The auto-signal-optimizing transducer assembly as set forth in claim 1, in which the transducer component comprises:
lens for focusing said transmitted and received ultrasound energy.

5. The auto-signal-optimizing transducer assembly as set forth in claim 1, comprising:
a) a volume of coupling agent configured for filling between the front face of the transducer component and the skin covering said adjacent body region when said assembly in attached to said skin surface portion, in which said coupling agent selected from the group consisting of:
i) an acoustic gel:
ii) RTV;
iii) Polyurethane:
iv) A clear spackling gel.

6. The auto-signal-optimizing transducer assembly as set forth in claim 1 futher configured to transmitting additional ultrasound to, and additional receiving ultrasound echo signals returned from, a $2^{nd}$ blood vessel disposed in a patient's body region in which said $2^{nd}$ blood vessel is oriented at a $2^{nd}$ vessel elevation angle relative to the skin surface, the auto-signal-optimizing transducer assembly further comprising:
a) a $2^{nd}$ transducer assembly for transmitting said additional ultrasound to, and receiving said additional ultrasound echo signals returned from, said $2^{nd}$ blood vessel, said second transducer assembly comprising:
i) $2^{nd}$ ultrasound transducer component having a $2^{nd}$ front face that transmits said additional ultrasound along a $2^{nd}$ scanning plane and receives said additional ultrasound echo signals returned along said $2^{nd}$ scanning plane;
ii) $2^{nd}$ signal connection means for coupling said $2^{nd}$ transducer to said ultrasound generator and processor unit that excites said $2^{nd}$ transducer to transmit said additional ultrasound and processes said additional returned ultrasound echo signals received by said $2^{nd}$ transducer component;
(1) $2^{nd}$ securing means for detachably and repeatably holding said $2^{nd}$ transducer component adjacent to said $2^{nd}$ body region and oriented with said $2^{nd}$ scanning plane disposed at a $2^{nd}$ transducer elevation angle relative to said $2^{nd}$ skin surface, in which said $2^{nd}$ transducer elevation angle is fixed to optimize said additional returned echo signals from said $2^{nd}$ blood vessel.

7. The auto-signal-optimizing transducer assembly as set forth in claim 1, in which said transducer component is divided into a CW transmitting portion and a CW receiving portion, wherein said ultrasound generator and processor unit continuously excites said CW transmitting portion transducer to continuously transmit CW ultrasound and processes returned CW ultrasound echo signals received by said CW receiving portion.

8. The auto-signal-optimizing transducer assembly as set forth in claim 1, in which said housing holder attachment means comprises:
a) a layer of adhesive material on said lower wing surface suitable for removably attaching said wings to said skin surface portion;
b) a strong, thin, flexible and magnetically active retainer tape comprising:
i) an upper and lower surface, in which said tape is formed such that said upper tape surface proximally contacts and magnetically holds to said holder wings when said holder wings are made of complementary magnetically active material,
ii) wherein said lower tape surface comprises an adhesive layer suitable for removably attaching said tape to said skin surface portion;

c) a retainer window formed in said retainer tape to be coextensive with said housing body opening when said housing body is fitted within said housing body holder.

9. The auto-signal-optimizing transducer assembly as set forth in claim 2, in which said ultrasound echo signal process is adapted to search for, identify and track an optimum signal at an optimum deflection angle, within said deflection range according to a signal optimizing algorithm, whereby said assembly continuously measures and monitors an optimum ultrasound signal from said blood vessel at an optimum azimuth deflection angle independent of the movement of said blood vessel relative to said adjacent skin surface.

10. The auto-signal-optimizing transducer assembly as set forth in claim 4, in which a focusing effect is achieved by curving a piezo-electric material into desired region of interest on said acoustic lens.

11. The auto-signal-optimizing transducer assembly as set forth in claim 4, in which said acoustic lens is made of RTV.

12. The auto-signal-optimizing transducer assembly as set forth in claim 5 further comprising conductivity electrodes mounted inside said housing body and electrically contacting said coupling agent and electrically connected to remote conductivity measuring equipment for the purpose of monitoring coupling agent conductivity so that ultrasound scanning can be terminated if the coupling agent conductivity is lower than a predetermined value.

13. The auto-signal-optimizing transducer assembly as set forth in claim 6, wherein said transducer is configured to be mounted on one side of a patient's neck adjacent to a first carotid artery, and said $2^{nd}$ transducer is configured to be mounted on the other side of said patient's neck adjacent to the other carotid artery.

14. An ultrasound transducer assembly comprising:
a) an ultrasound transducer unit presenting an outward facing ultrasound scanning array on one side;
b) a body portion attachment means configured to detachably securing said body portion attachment means proximal to a fixed location and fixed orientation at a skin surface portion of a body region of a patient;
  i) transducer unit securing means for detachably and repeatedly securing said transducer unit to said body portion attachment means, in which said transducer unit securing means comprises:
    c) a housing body fixedly encapsulating, protecting and holding said transducer unit at said fixed location and fixed orientation with said scanning array disposed adjacent to and facing said skin surface portion; said housing body comprising:
      i) a top with spaced apart, parallel front and back edges extending between two spaced apart, parallel side walls
      ii) longitudinal ribs extending along opposite parallel side walls;
      iii) a perpendicular bottom face between the two opposite side walls presenting an opening for the ultrasound and received ultrasound signals to pass between the face of said transducer unit and said skin surface when said housing body is adapted to secure to said body portion;
    d) a housing body holder comprising:
      i) a lateral base member;
      ii) a rigid open rectangular channel with a back wall between two parallel side walls extending upright from said lateral base member, the holder side walls spaced apart to receive said housing body with said parallel side walls fitted closely within, the inside of the two holder side walls having opposing grooves formed to slidingly receive and retain said longitudinal ribs of said housing body when said housing body is fitted against said back wall of said channel;
      iii) the lateral base member forming an opening co-extensive with said fitted housing opening;
      iv) opposing, thin lateral wings having respective upper and lower surfaces, said wings extending away from said holder opening to distal free ends, said wings shaped to fit closely proximal on said skin surface portion when attached adjacent to said body region, and having sufficient strength to reliably maintain said holder and said housing body in a fixed position and orientation when attached to said skin surface portion;
    e) housing body holder attachment means configured to attach said lower surface of said lateral wings to said skin surface portion;
    f) signal connection means for connecting said array to a distal signal generating and signal processing unit for communicating ultrasound excitation signals from said processing unit to said array for transmitting ultrasound into said body region through said skin surface portion and for communicating resulting ultrasound echo signals received by said array from said body portion back to said processing unit.

15. The ultrasound transducer assembly set forth in claim 14 wherein:
a) said scanning array is adapted to cooperate with said generating and processing unit such that:
  i) said scanning array generates an ultrasound beam that cyclically sweeps at a scanning rate over a maximum deflection angle range in a scanning plane oriented at a fixed elevation angle relative to said skin surface portion.

16. The ultrasound transducer assembly set forth in claim 14, wherein:
a) said generating and processing unit is adapted to process said echo signals during one or more cycles of said sweep to determine a maximum ultrasound Doppler signal amplitude for each one of said one or more cycles.

17. The ultrasound transducer assembly as set forth in claim 14, in which said housing holder attachment means comprises:
  i) a layer of adhesive material on said lower wing surface suitable for removably attaching, said wings to said skin surface portion;
  ii) a strong, thin, flexible and magnetically active retainer tape comprising:
    (1) an upper and lower tape surface, in which said upper tape surface is formed to proximally contact and magnetically hold to said holder wings when said holder wings are made of complementary magnetically active material,
    (2) wherein said lower surface comprises an adhesive layer suitable for removably attaching said tape to said skin surface portion;
  i) a retainer window formed in said retainer tape to be coextensive with said housing body opening when said said housing body is fitted within said housing body holder.

18. The ultrasound transducer assembly as set forth in claim 15, wherein said generating and processing unit computes a blood flow parameter using one or more of said maximum ultrasound Doppler signal amplitudes.

19. The ultrasound transducer assembly as set forth in claim 15, wherein said generating and processing unit computes an average value for a blood flow parameter using a plurality of said maximum ultrasound Doppler signal amplitudes.

20. The ultrasound transducer assembly as set forth in claim 15, wherein said generating and processing unit computes a trend line for a blood flow parameter using a plurality of said maximum ultrasound Doppler signal amplitudes.

21. The ultrasound transducer assembly as set forth in claim 6, wherein:
   a) said ultrasound generator and processor unit computes at least one difference signal between said processed returned ultrasound echo signals and said processed additional returned ultrasound echo signals and provides a notice to be apprehended when said at least one difference signal exceeds at least one predetermined limit value.

22. The ultrasound transducer assembly as set forth in claim 21, in which said notice comprises:
   a) an aural alarm to be heard by attending personnel;
   b) a visual alarm to be seen by attending personnel;
   c) a signal for transmission to equipment for notifying monitoring personnel at a remote location;
   d) a signal coupled to automatic intervention equipment configured to provide automatic interventional treatment to reduce said difference signal below said predetermined limit value.

23. An auto-signal-optimizing medical ultrasound measurement and monitoring system comprising:
   a) said auto-signal-optimizing transducer assembly as set forth in claim 9,
   b) wherein said ultrasound generator and processor unit is a diagnostic medical ultrasound apparatus,
   c) wherein said transducer assembly and said ultrasound apparatus configured to enable said diagnostic medical ultrasound apparatus to receive an initial optimum ultrasound Doppler return signal from a blood vessel in said body region and provide an initial optimum blood vessel related metric value or an initial optimum displayed image by locating, orienting in azimuth and securing said auto-signal-optimizing transducer by said securing means on a skin surface portion adjacent to said blood vessel in said body region.

24. The auto-signal-optimizing medical ultrasound measurement and monitoring system as set forth in claim 23, wherein said diagnostic medical ultrasound apparatus is further adapted to process said returned ultrasound echo signals to search for, identify and track an optimum Doppler signal at an optimum deflection angle, within said deflection range according to a signal optimizing algorithm, whereby said system provides the capability for said diagnostic medical ultrasound instrument to provide continuous, unattended monitoring of said blood vessel related metric or display of said image by said mounting, locating and orienting.

25. The auto-signal-optimizing medical ultrasound measurement and monitoring system as set forth in claim 24, wherein said signal optimizing algorithm selects said optimum deflection angle for a maximum.

26. The ultrasound transducer assembly as set forth in claim 22, in which said CW transmitting portion is one half of said array and said CW receiving portion is the other half of said array.

* * * * *